(12) United States Patent
Mark

(10) Patent No.: US 11,246,668 B1
(45) Date of Patent: Feb. 15, 2022

(54) MINIMALLY INVASIVE SURGICAL TOOL WITH ASYMMETRIC GEAR ASSEMBLY

(71) Applicant: ESSENTIAL MACHINES, INC., Santa Clara, CA (US)

(72) Inventor: Alexander Mark, Santa Rosa, CA (US)

(73) Assignee: YIJIAHE (SINGAPORE) PTE. LTD., Singapore (SG)

( * ) Notice: Subject to any disclaimer, the term of this patent is extended or adjusted under 35 U.S.C. 154(b) by 0 days.

(21) Appl. No.: 17/378,388

(22) Filed: Jul. 16, 2021

(51) Int. Cl.
*A61B 34/30* (2016.01)
*B25J 17/02* (2006.01)
*A61B 17/00* (2006.01)

(52) U.S. Cl.
CPC ........ *A61B 34/30* (2016.02); *A61B 17/00234* (2013.01); *B25J 17/02* (2013.01); *A61B 2034/305* (2016.02)

(58) Field of Classification Search
CPC .............. A61B 34/30; A61B 17/00234; A61B 2034/305; A61B 2034/715; A61B 2017/00314; A61B 2017/00318; A61B 2017/00323; A61B 2017/00327; A61B 34/71; B25J 17/02; B25J 9/102; B25J 9/126; B25J 17/0241; B25J 17/0258; F16H 1/14; F16H 1/203; F16H 35/06
USPC ........................................................... 606/1
See application file for complete search history.

(56) References Cited

U.S. PATENT DOCUMENTS

| | | | |
|---|---|---|---|
| 5,013,317 A * | 5/1991 | Cole | A61B 17/1703 606/96 |
| 10,220,522 B2 * | 3/2019 | Rockrohr | A61B 34/71 |
| 11,141,156 B2 * | 10/2021 | Shelton, IV | A61B 17/068 |
| 2006/0219065 A1 * | 10/2006 | Jinno | A61B 34/71 81/383 |
| 2008/0039256 A1 | 2/2008 | Jinno et al. | |
| 2008/0046122 A1 * | 2/2008 | Manzo | A61B 34/71 700/245 |
| 2009/0039819 A1 * | 2/2009 | Wilson | B25J 17/0275 318/568.12 |
| 2009/0216249 A1 | 8/2009 | Jinno et al. | |
| 2012/0245569 A1 * | 9/2012 | Papac | A61F 9/00763 606/1 |
| 2013/0131695 A1 * | 5/2013 | Scarfogliero | A61B 34/30 606/130 |

(Continued)

FOREIGN PATENT DOCUMENTS

| | | |
|---|---|---|
| WO | 2017018048 | 2/2017 |
| WO | 2018081931 | 5/2018 |

*Primary Examiner* — Aaron F Roane
(74) *Attorney, Agent, or Firm* — Faegre Drinker Biddle & Reath LLP

(57) ABSTRACT

A surgical tool having a compact design is disclosed. The tool has a first set of prongs disposed along a first axis, a second set of prongs disposed along a second axis different from the first, and an asymmetric gear set. The gear set includes a rotatable first drive gear disposed on one of the first set of prongs and a rotatable first actuator gear disposed on one of the second set of prongs. The first drive gear is configured to drive the first actuator gear, forming a first gear pair. The gear set also includes a rotatable second drive gear disposed on one of the first set of prongs and a rotatable second actuator gear disposed on one of the second set of prongs. The second drive gear is configured to drive the second actuator gear, forming a second gear pair. The first gear pair and the second gear pair have different diameters.

21 Claims, 17 Drawing Sheets

(56) References Cited

U.S. PATENT DOCUMENTS

| | | | |
|---|---|---|---|
| 2014/0213409 A1* | 7/2014 | Yoon | B25J 9/1025 |
| | | | 475/343 |
| 2017/0014197 A1 | 1/2017 | McCrea et al. | |
| 2020/0077994 A1 | 3/2020 | Shelton, IV et al. | |
| 2020/0129253 A1 | 4/2020 | Jackson et al. | |
| 2020/0130201 A1 | 4/2020 | Butt et al. | |
| 2020/0254608 A1* | 8/2020 | Yeung | B25J 17/0241 |

\* cited by examiner

MINIMALLY INVASIVE SURGICAL TOOL WITH ASYMMETRIC GEAR ASSEMBLY

TECHNICAL FIELD

The present disclosure is related to surgical instruments for minimally invasive surgical procedures. In particular, the present disclosure is related to an end effector instrument for use with a robotic surgery system.

BACKGROUND

Robotic surgery enjoys a growing market share in a wide variety of medical procedures requiring surgery. The robotic system provides a controlled tool that a surgeon can manipulate using a control interface. Surgical robots may be designed to control a wide variety of end effectors (tools). These tools generally mimic the non-robotic tools available to a surgeon when surgery is done by manual methods without minimally invasive tools. Tools of this kind tend to have multiple joints or bending points in order to achieve a small size and increased flexibility. Likewise reducing the diameter of the tool and the drive mechanism is a goal for gaining access to smaller and more confined regions of the body.

SUMMARY

One area of interest in the field of end effector tools for surgical robots is a device that can mimic the human hand in range of motion and also grasp objects. Similar end effectors may also be useful in a variety of minimally invasive procedures conducted with manually operated tools. Some embodiments of the present disclosure may meet some of the desired trends of the industry by creating a tool with greater flexibility and smaller in operating size.

A surgical tool with an asymmetric gear assembly is described herein, along with methods and examples of use. The asymmetric gear assembly allows for the surgical tool to have a reduced size compared to other surgical tools used for similar tasks. In an embodiment, the asymmetric gear assembly may provide a reduced cross section, or a reduced overall length, of the present surgical tool as compared to other existing surgical tools of the same kind.

The reduced size of the present surgical tool may lend this tool to a greater range of surgical procedures.

In an embodiment, there may be an apparatus for use with a robotic tool, the apparatus forming a joint using an asymmetric gear assembly, for example. The apparatus in some examples includes a first set of prongs disposed along a first axis, a second set of prongs disposed along a second axis and an asymmetric gear set. The second axis is different from the first axis. The asymmetric gear set has a first rotatable drive gear that is disposed on one of the first set of prongs and has a first diameter. A first rotatable actuator gear of the asymmetric gear set is disposed on one of the second set of prongs and has the same diameter as the first drive gear. The first drive gear and the first actuator gear may be in mechanical communication such that the first drive gear is configured to drive the first actuator gear, the first drive gear and the first actuator gear forming the first gear pair. A rotatable second drive gear of the asymmetric gear set is disposed on one of the first set of prongs and has a second diameter. The second diameter is different from the first diameter. A rotatable second actuator gear of the asymmetric gear set is disposed on one of the first set of prongs and also has the same diameter as the second drive gear. The second drive gear and the second actuator gear may be in mechanical communication with each other such that the second drive gear is configured to drive the second actuator gear. The second drive gear and the second actuator gear together form the second gear pair.

The apparatus in some examples may include a restraint mechanism which restrains axial movements of the asymmetric gear set. The restraint mechanism may include a block and a housing having at least one aperture. A wrist gear is mechanically engaged to one of the first set of prongs through the at least one aperture. The first set of prongs may have a first prong and a second prong. The first prong and the second prong are disposed on opposite sides of the block. In some examples, the second set of prongs may have a third prong and a fourth prong which may be disposed on opposite sides of the block, such that the first and second sets of prongs occupy different sides of the block from each other. In some examples, the first and second axles may be substantially orthogonal to each other. In some examples, the first drive gear may be rotatably mounted on the first prong, the first actuator gear may be rotatably mounted on the third prong. The first drive gear and the first actuator gear may be positioned substantially orthogonal to each other. The second drive gear may be rotatably mounted on the second prong, the second actuator gear may be rotatably mounted on the fourth prong, and the second drive gear and the second actuator gear may be positioned substantially orthogonal to each other. The apparatus may also have a housing having at least one aperture such that a wrist gear may be mechanically engaged to the first prong. The housing may be configured to confine the asymmetric gear set between the housing and the block so each gear rotates on its respective prong while minimizing the axial movement of each gear on each prong. The first gear set may be asymmetrical to the second gear set in size and/or shape with respect to a dividing line defined between the first gear set and the second gear set.

In some examples, the first drive gear is movable by a first drive cable, and the first drive cable is configured to connect to the first drive gear to a first drive spool. The second drive gear is movable by a second drive cable, and the second drive cable is configured to connect to the second drive gear to a second drive spool. In some examples, the first actuator gear is configured to connect to a first actuator or the second actuator gear is configured to connect to a second actuator. In some examples, the apparatus further includes a wrist cable configured to connect the wrist gear to a wrist drive spool. In some examples, the apparatus further includes a rotatable base mechanically coupled to the asymmetric gear set. In some examples, the apparatus includes a base cable configured to connect the rotatable base to a base spool. The base may include a first tab and a second tab, and the apparatus is configured to rotate about the first axis while rotationally engaged to the first and second tabs. In some examples, one or more of the first drive gear, the first actuator gear, the second drive gear, or the second actuator gear of the asymmetric gear set include one or more beveled gears. In some examples, the first diameter is smaller than the second diameter. In some examples, the first drive gear or the first actuator gear of the first gear pair is made of a different material than the corresponding second drive gear or the second actuator gear of the second gear pair. In some examples, the joint is movable in four degrees of freedom (DOF).

In another embodiment, there may be a minimally invasive surgical tool with a base and a joint, as well as a first driver gear, a second drive gear, a first actuator gear, a second actuator gear, a first actuator, and a second actuator. A joint may have a first set of prongs disposed along a first axis and a second set of prongs disposed along a second axis, the second axis being different from the first axis. A first drive gear may be positioned on the first prong of the first set of prongs, and the first drive gear may have a first diameter. A second drive gear may be positioned on a second prong of the first set of prongs. The second drive gear may have a second diameter that is different from the first diameter. A first receiver gear may be positioned on a first prong of the second set of prongs, the first receiver gear having the same diameter as the first drive gear. A second receiver gear may be positioned on a second prong of the second set of prongs, the second receiver gear having the same diameter as the second drive gear. The surgical tool may also have a first mechanism, or actuator, coupled to the first receiver gear, the first mechanism rotatable in response to movement of the first or second drive gear, and the first or second receiver gear. The surgical tool may also have a second mechanism coupled to the second receiver gear, the second mechanism rotatable in response to movement of the first or second drive gear. The base may have a set of tabs extending therefrom. The set of tabs may be arranged to contain an axle. The base is rotatable about a third axis, the third axis being different from the first axis and the second axis, and the first set of prongs are mechanically engaged to the set of tabs. The first and second mechanisms may be movable in six DOF by rotating the first and second mechanisms around the first, second or third axis, for examples.

In some examples, the second set of prongs may be substantially orthogonal to the first set of prongs. In some examples, a housing may be fittingly engaged to the joint such that the first pair of prongs and the second pair of prongs may protrude from the housing when the joint is placed within the housing. In some examples, a housing having at least one aperture may also be fittingly engaged. For example, a wrist gear can be mechanically engaged to one of the first set of prongs through the at least one aperture. For example, the first prong and the second prong may be disposed on opposite sides of the joint. In some examples, the base has a proximal end and a distal end, the pair of tabs extending distally. In some examples, the first diameter is greater than the second diameter, whereas in some examples, the second diameter is greater than the first diameter.

In another embodiment, there may be a surgical system including a surgical apparatus. The surgical apparatus includes a first set of prongs disposed along a first axis, a second set of prongs disposed along a second axis, the second axis being different from the first axis, and an asymmetric gear set. The asymmetric gear set may include a rotatable first drive gear disposed on one of the first set of prongs, a rotatable first actuator gear disposed on one of the second set of prongs. The first drive gear and first actuator gear are in mechanical communication such that the first drive gear is configured to drive the first actuator gear, the first drive gear and the first actuator gear forming a first gear pair, a rotatable second drive gear disposed on one of the first set of prongs, and a rotatable second actuator gear disposed on one of the second set of prongs. The second drive gear and the second actuator gear are in mechanical communication such that the second drive gear is configured to drive the second actuator gear, the second drive gear and the second actuator gear forming a second gear pair.

In some examples, the surgical system further includes a first drive cable movably connecting the first drive gear to a first drive spool, a second drive cable movably connecting the second drive gear to a second drive spool, and a controller operably coupled with the first drive spool and the second drive spool. The controller may be capable of determining a rotation and movement of each of the first gear pair and the second gear pair based on a respective size of the first gear pair and the second gear pair, and providing operation control of the first drive cable and the second drive cable based on the determined rotation of the first and second drive spools. The first and second drive spools may have encoders. Additional encoders may measure the rotation of the first and second drive gear, or the first and second actuator gear.

In some examples, the surgical system further includes a first motor assembly electrically coupled with the controller and mechanically coupled with the first drive cable, the first motor assembly configured to control the first drive cable based on the operation control provided by the controller, and a second motor assembly electrically coupled with the controller and mechanically coupled with the second drive cable, the second motor assembly configured to control the second drive cable based on the operation control provided by the controller. In some examples, the surgical system further includes a block as well as a housing having at least one aperture. A wrist gear is mechanically engaged to one of the first set of prongs through the at least one aperture. The first set of prongs including a first prong and a second prong. The first prong and the second prong are disposed on opposite sides of the block. In some examples, the first drive gear has a first diameter and the second drive gear has a second diameter. The first diameter is different from the second diameter.

BRIEF DESCRIPTION OF THE DRAWINGS

The above-mentioned and other features of this disclosure and the manner of obtaining them will become more apparent and the disclosure itself will be better understood by reference to the following description of embodiments of the present disclosure taken in conjunction with the accompanying drawings.

DETAILED DESCRIPTION

Figure 1:
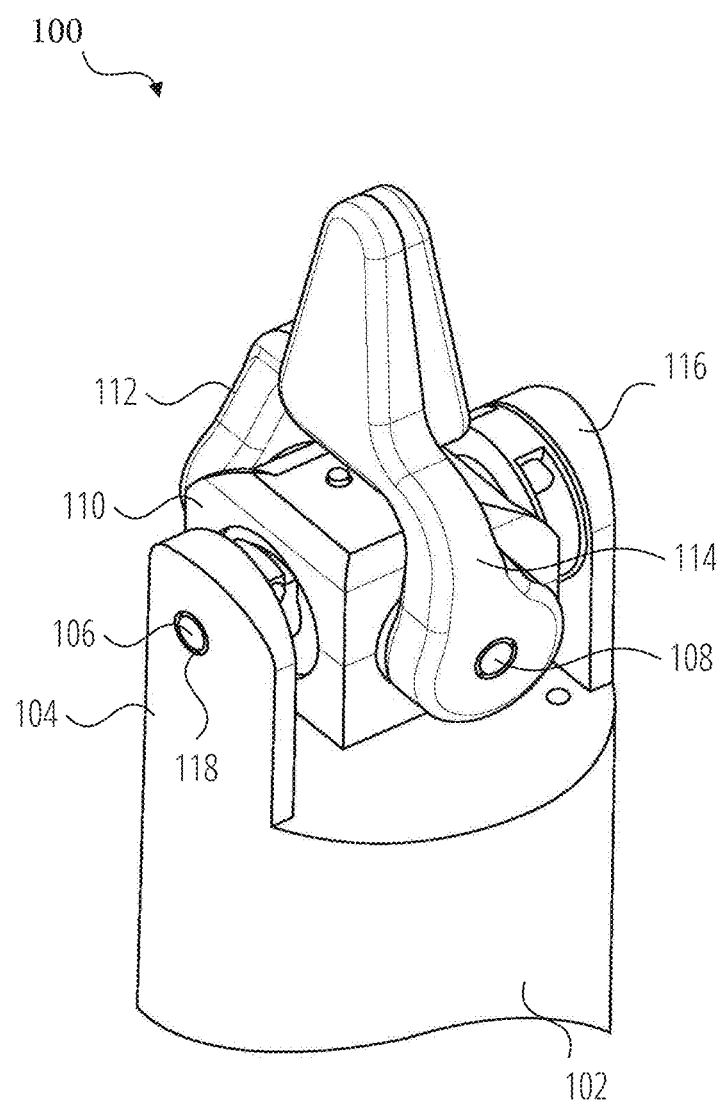
FIG. 1 illustrates an aspect view of the surgical instrument in accordance with an embodiment.

Described herein are an asymmetric gear set for use with a surgical tool. The asymmetric gear set may use four gears confined within a housing and arranged around a cross or X shaped center. The center may be a block or other structure on which the four gears may abut. The block may have four (4) sides arranged around its perimeter. The top and bottom may be flat and smooth, or curved or other shapes. In an embodiment, the block may simply be a cube, or substantially cube shaped. Extending from the block may be four (4) prongs or rods that function like axles for rotating gears. The prongs may be positioned one on each of the four (4) sides of the perimeter of the block. A first pair of prongs may be on opposite sides of the block, and in a straight line. These prongs in a line may define a first axis and may form a first axle. The other two prongs may be on the remaining two sides, again opposite of each other, and in line, to define a second axis, and form a second axle.

The four gears may be axially loaded onto the four prongs, so there may be one gear on each prong. Two of the gears that are adjacent to each other, but placed orthogonal to each other, may mesh together and form a first gear pair. The first gear pair may be two beveled gears that may mesh with each other while the gears rotate at substantially a right angle from each other. Each of the first two gears in the first gear pair may have the same diameter, shape or other physical dimensions. Any variation between the two gears may be acceptable as long as the two gears may transfer mechanical force to each other in a reliable and predictable manner. The other two gears may be adjacent to each other and rest in an orthogonal position on the other two prongs. The second gear set may be positioned so the individual gears of the second gear set may be a different size from the first gear set. The second gear set may be larger in diameter, or in some other physical parameter. The difference in size or shape for the first gear set and the second gear set may be useful to allow the two gear sets to rotate without interfering with each other. The ability of all four (4) gears to rotate at the same time, and while each gear axle rests in the same plane, provides a construction where the four (4) gears may be positioned around a small center structure such as the block.

In various embodiments, the gears may be referred to as a first drive gear, a second drive gear, a first actuator gear and a second actuator gear. The first drive gear may be paired with the first actuator gear and form may the first gear pair. The second drive gear may be paired with the second actuator gear and may form the second gear pair. The first and second drive gears may be driven by cables which may be attached to motors, or driven by pulleys, which are in turn driven by motors. In some embodiments, a group of three motors may be used to drive the asymmetric gear assembly. In some embodiments, a fourth motor may be used to drive the surgical tool incorporating the asymmetric gear assembly. In some embodiments, a pulley assembly may be housed in a separate container from the motor assembly. Torque or mechanical force may be transferred from the motors to the pulleys using a variety of simple or complex links. The separation may allow the motor assembly to remain clean and free of biological tissue and/or surgical waste. The pulleys may be contaminated, but may be cleaned. The surgical tool may be reusable after being cleaned and sterilized, or the surgical tool may be disposable (single use medical device). The pulley assembly may also be disposable.

In various embodiments, the block, prongs and gears may be contained within a housing. The housing may have an asymmetric shape so as to be somewhat form fitted around each gear, so as to minimize the axial play of each gear as it rotates on its respective prong. In some embodiments, the block and the housing may form the parts of a restraining mechanism. In other embodiments, other elements may form the parts of a restraining mechanism. Each drive gear has a gear component that may be inside the housing, and a drive component that may extend outside the boundaries of the housing. The drive component of the two drive gears may receive a drive cable, which may be secure to the drive component. Alternatively, the drive cable may not be fixed to the drive component and rotate without limitation. In some embodiments the drive component may have more than wind of the cable on the drive component or the drive pulley.

In some embodiments, a wrist driver, or wrist gear, may be attached to the first prong, outside the housing, and next to the first drive gear. The first drive gear may rotate freely on the first prong, while the wrist driver may be fixed to the first prong. A drive cable may extend from a wrist motor or wrist pulley, to the wrist driver. When the wrist motor or pulley may be activated, the wrist driver may rotate and may rotated the entire asymmetric gear assembly on the first axis.

In various embodiments, the first and second actuator gears may be mechanically engaged with, fixedly attached to, or incorporated into actuators. The actuators may be simple physical or mechanical elements, such as opposing grippers, opposing clamps, opposing blades (scissors), and so on. In some embodiments, the actuators may be sensor, such as a nerve detector, a temperature probe, an ion detector, a smoke analyzer, and so on. Various control wires, sensor wires and/or power wires may run through the base of the surgical tool toward the robot arm and robot body. In some embodiments, the electronic components may be battery powered and communicate wirelessly.

In some embodiments, the asymmetric gear assembly and the actuators may be mounted along the axis defined by the first and second prong. The first and second prongs may be engaged with a pair of tabs extending from a rotatable base. The various drive cables, control wires, power lines, and any other components that may need to have a physical connection to something proximal to the surgical tool, may be routed through the base. The base may rotate on an axis generally perpendicular to the plane of the base face, forming another degree of motion for the surgical tool. The base surface may be sloped, to allow for a greater range of motion of the actuators as they rotate on the axis defined by the first and second prongs.

In some embodiments, a series of motion encoders may be incorporated to either the motors, the drive pulleys or the different gears. In this manner, a computer controller may accurately determine the rotation and movement of each element of the asymmetric gear assembly and the surgical tool. In some embodiments, these may be mechanical encoders. In some embodiments, these may be electromechanical encoders, in some embodiments, these may be optical or electromagnetic encoders. The motion information may be used by a computer controller, with a software controller, specifically designed to operate the asymmetric gear assembly and the surgical tool described herein. The computer controller and software controller may project onto a display for a user, the position of the actuators of the surgical tool.

In various embodiments, the asymmetric gear assembly and the surgical tool may be made from any appropriate material. In some embodiments, the smaller of the two gear sets may be made from material that has higher tensile strength, higher density, or higher quality, so that the smaller gears may impart an equal amount of torque to the actuator connected to the smaller actuator gear, as compared to the larger gear set. In this manner the asymmetric drive assembly may be rated for mechanical work for each drive component. In some other embodiments. The load acceptable by the smaller gear set may be less than the larger gear set, in this case the rating for the load or work of the surgical tool may be limited by the smaller drive component. Various metals such as stainless steel, titanium, palladium and so on, may be used for any one or more of the components. In some embodiments, various polymers may be used, such as polystyrene, polypropylene, polycarbonate, and so on. In some embodiments, the various components may be made from a ceramic material, ceramic alloy, ceramic composite or ceramic polymer. In other embodiments, the various components may be made from nanocomposites. The manufacture of any individual element may be made of any material, and different classes of materials may be mixed and matched freely.

In the various embodiments, the components of the asymmetric gear assembly and surgical tool may be made by various well-known processes, such as metal injection molding (MIM), computer numeric control (CNC) machining, electrical discharge machining, plastic injection molding and so on. Parts may be assembled by laser welding, adhesive bonding, ultrasonic welding, mechanical fastening and so on.

While the general and detailed description of the asymmetric gear assembly and surgical tool may be useful in understanding the present disclosure, these descriptions should not be taken as limiting, as various alternative and equivalent embodiments may come to light upon review of the present disclosure. In review of the various figures, the views shown are provided to highlight or describe the various components, elements and features of the design. The drawings are not to be taken as being to scale, or an absolute representation of the design and disclosure, of which many alternate embodiments are possible.

In the descriptions of the various embodiments, elements, components or assemblies may be described as substantially in line, or in relation with something. The use of substantially may be taken as meaning a variation of +/−15% of an absolute measure, or 15 degrees from an angle. A joint may be substantially orthogonal, which may allow for +/−15 degrees from normal. An element, object, assembly or component that may be substantially 100 cm long, may be 100 cm+/−15 cm (15%) unless context clearly indicates otherwise.

FIG. 1 depicts a schematic design of one example the instrument or surgical tool 100 in accordance with certain embodiments of the present disclosure. The surgical tool may have a base 102 supporting a pair of bracket arms, as shown in FIG. 1. A first bracket arm 104 and a second bracket arm 116 may be positioned on opposing sides of the base 102. The first bracket arm 104 and second bracket arm 116 may each have an aperture 118. The apertures in the bracket arms may be positioned in opposition from each other and may receive a first axle 106. The first axle 106 may be set in or through a first and second apertures 118 in the first bracket arm 104 and second bracket arm 116 respectively. A second axle 108 may define an axis of rotation for the first actuator 112 and second actuator 114. The various drive gears and actuator gears may be inside the housing 110.

In some embodiments, the drive cables may be positioned outside the housing, while the drive gears are positioned inside the housing 110. In some embodiments, the first axle 106 may function like a wrist, allowing the housing 110 and first actuator 112 and second actuator 114 to rotate around the axis of the first axle 106. In various embodiments, the first actuator 112 and second actuator 114 may be replaced with a wide variety of surgical tools, probes or sensors.

Figure 2:
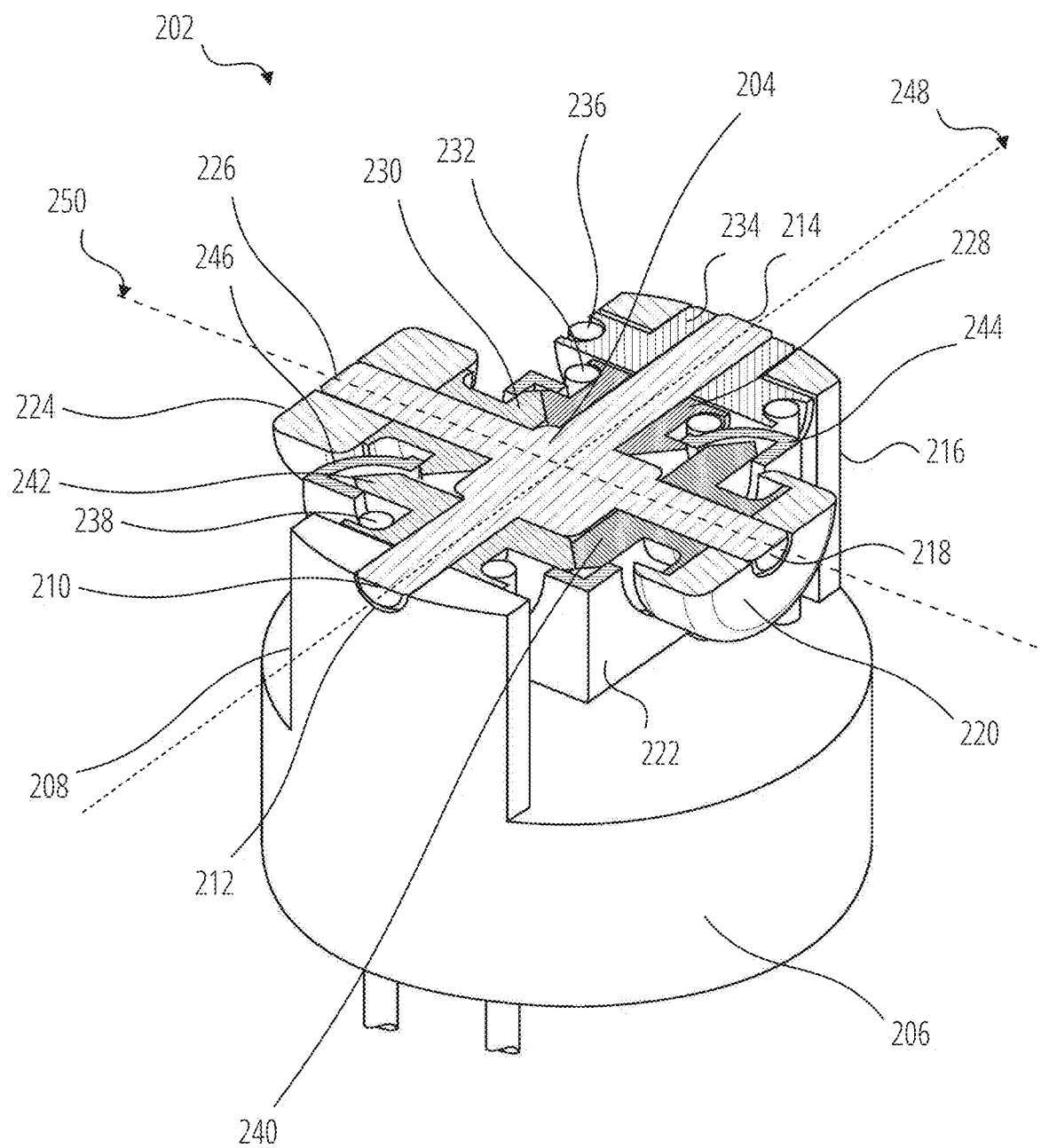
FIG. 2 illustrates a cross section view of the surgical instrument according to an embodiment.

FIG. 2 depicts a cut away view of a schematic design of one example of a surgical tool 202, in accordance with certain embodiments of the present disclosure. In an embodiment, the surgical tool 202 may have a base 206 with a pair of opposing brackets. A first bracket 208 and a second bracket 216 may be positioned on opposite sides of the base 206. The first bracket 208 may have a first aperture 212 for receiving a second prong 210. The prong may be a rod, or similarly shaped object which may be seated in the first aperture 212 and able to rotate freely within the first aperture 212. A joint 204 may be positioned substantially in the middle or in any space between the brackets. The joint 204 may have the second prong 210 and a first prong 214 attached to the joint, with the first and second prongs arranged in an axial alignment on opposite ends of the joint. The prongs in an axial alignment may form a first axis 248. The first axis 248 may function as a wrist for the surgical tool 202. The rest of the elements of the tool reside on, around or attached to the joint 204 and the prongs attached to the joint, either directly or indirectly, and may be independent of the base and the brackets.

In an embodiment, a joint 204 having four (4) prongs may be positioned between the first bracket 208 and the second bracket 216. The joint 204 may be a block with a second prong 210 and a first prong 214 in a generally axial alignment and on opposite sides of the joint 204. The joint 204 may have a third prong 218 and a fourth prong 226 in a generally axial alignment and on opposite sides of the joint 204. The first prong 214 and the second prong 210 may define the first axis 248, while the third prong 218 and the fourth prong 226 may define a second axis 250. The individual prongs may vary in size and diameter. It is not required that the prongs have a uniform size or length compared to each other. The first axis 248 and the second axis 250 may be positioned in a generally orthogonal orientation with respect to each other. In some embodiments, the prongs may be rods, or shafts extending through the joint block. In some embodiments, the prongs may be spindles, axles, pins or any element that may allow a gear to rotate around it.

In an embodiment, the joint 204 provides the main axis of rotation for the wrist and for the actuators. In an embodiment, a wrist driver 234 may be fixedly attached to the first prong 214. The wrist driver 234 may have a wrist cable 236 attached to it. The wrist cable 236 may be actuated by a motor, causing the wrist cable 236 to rotate the wrist driver 234. The rotation of the wrist driver 234 may cause the second prong 210 and first prong 214 and joint 204 to rotate about the first axis 248. In various embodiments, the second prong 210 and the first prong 214 may be part of the joint 204, and fabricated from a single block of material. In some examples, the first and second prongs may be in fixed positions with the joint after assembly. In some embodiments, the joint 204 may be referred to herein as the cross base. The term cross base and joint may be used interchangeably.

In an embodiment, a pair of actuator gears may rotate about the first axis 248. A first drive gear 228 and a second actuator gear 240 may be rotationally mounted on the first axis 248. The first drive gear 228 may be a different diameter than the second actuator gear 240. In an embodiment, the first drive gear 228 may be rotationally connected to a first actuator gear 230. A first actuator cable 232 may be driven by a motor and fixed to the first drive gear 228. The movement of the first actuator cable 232 may cause the first drive gear 228 to rotate back and forth, and also cause the rotation of the first actuator gear 230. The first actuator gear 230 may be fixedly attached to a first actuator 224, such that when the first actuator gear 230 rotates over the fourth prong 226, the first actuator 224 moves in direct relation to the first actuator gear 230.

In various embodiments, the first drive gear 228 and the wrist driver 234 may be positioned adjacent to each other on the same prong. The wrist driver 234 may be fixedly attached to the first prong 214, so when the wrist driver 234 rotates, the first and second prongs also rotate. The first drive gear may be rotationally mounted on the first prong 214, so when the first prong 214 rotates in response to motion by the wrist driver 234, the first drive gear 228 may remain stationary. That is the first drive gear 228 may be mounted on the first prong 214 in a manner so that the first drive gear 228 does not rotate when the second prong rotates. In some embodiments, the first drive gear 228 may have a beveled gear and a region extending away from the beveled gear, the region extending away may be slotted or shaped to receive the first actuator cable 232. In some embodiments, the first actuator cable 232 may be fastened to the first drive gear 228. The cable may be fastened by using a crimping fastener that locks a section of the cable to the gear such that the gear may be rotated equally in each direction. In some embodiments, the cable may wrap around the gear more than once, so the gear may be rotated a full 360 degrees with causing the cable fasten point to be a limit on rotation.

The first drive gear 228 may be mechanically engaged to a first actuator gear 230. The first actuator gear 230 may be fixedly attached to the first actuator 224, such that the first drive gear 228 may control the movement of the first actuator 224 vie the first actuator gear 230. The first actuator gear 230 and the first actuator 224 may freely rotate over the fourth prong 226, such that the first actuator 224 may be moved independently of how the orientation of the fourth prong 226 and second axis 250 may move as driven by the wrist driver 234.

In some embodiments, a second drive gear 242 may be rotationally mounted on the second prong 210. The second drive gear 242 may have a second actuator cable 238. The second actuator cable 238 may have a section that may be fastened to the second drive gear 242, by crimping or other fastening device or techniques as may be well understood in the art. In some examples, the cable may be welded, soldered, or crimped to the second drive gear 242. In some embodiments, the cable may be replaced with a micro chain and sprocket gear arrangement. In still other embodiments, the gears of the tool may be moved using a magnetic driver. The second drive gear 242 may drive a second actuator gear 240 which may be fixedly attached to or mechanically engaged with a second actuator 220. The second actuator gear 240 and second actuator 220 may freely rotate over the third prong 218. In various embodiments, the movement of the first actuator 224 and the second actuator 220 may be moved independently from one another, so the actuators may operate in two different motions, in cooperative motion, as a single tool with two components (like a clamp, scissors or tweezers) or independently as two different tools (as a probe and a cutting tool).

In some embodiments, the various gear elements of the surgical tool may be positioned within a housing 222. In an embodiment, the housing 222 contains the joint 204 and a portion of each of the prongs that connects or is closest to the joint 204. The gear components of the first drive gear 228, first actuator gear 230, second drive gear 242 and second actuator gear 240 are arranged orthogonal to each other within the confines of the housing 222. The joint 204 and the four prongs may be sized to fit the four gear elements in orthogonal relationship to each other, with the housing 222 holding the four gear elements in place so they gears do not slip or slide of their respective prongs when the gears are in motion. The housing may also provide a limitation on the axial play of each gear. In some embodiments, the housing may help keep the first drive gear 228 and first actuator gear 230 in contact and promote engagement. In some embodiments the housing may help the second drive gear 242 and the second actuator gear 240 in contact and promote engagement. The housing 222 may have various curved features adapted for fitting around the gear elements which may be of different size.

In an embodiment, the first drive gear 228 may have a smaller diameter than the second drive gear 242. In an embodiment the first actuator gear 230 may have a smaller diameter than the second actuator gear. The first drive gear 228 and first actuator gear 230 may form the first drive assembly, while the second drive gear 242 and the second actuator gear 240 may form the second drive assembly. In an embodiment, having the first drive assembly and the second drive assembly being of different diameters (or size) may allow the first and second drive assembly to be positioned orthogonal to one another within the housing 222 and operate independently without interfering with one another. In some embodiments, the housing 222 may be adapted to accommodate a larger second actuator gear 240 by using a first housing protrusion 244, and a second housing protrusion 246 to accommodate the second drive gear 242. In various embodiments, the housing 222 shape may be adapted to accommodate different sizes or different shapes of the gears contained within. In some embodiments, the housing and block act together as a restraint mechanism, or as parts of the restraint mechanism, to contain the gears in a specific orientation, and provide a structure for the gears to operate together. In other embodiments, the block or housing may be substituted for other elements that perform as a restraint mechanism. The gears may have extensions or be connected to drive components (such as pulleys, spools, connectors and so on) to facilitate the driving of the gears by motor forces as detailed herein.

In some embodiments, the third prong 218 and fourth prong 226 may not be in a single axial alignment. The prongs may be purposely misaligned so the actuators do not come together or function as a single tool, but instead operate as independent tools.

Figure 3:
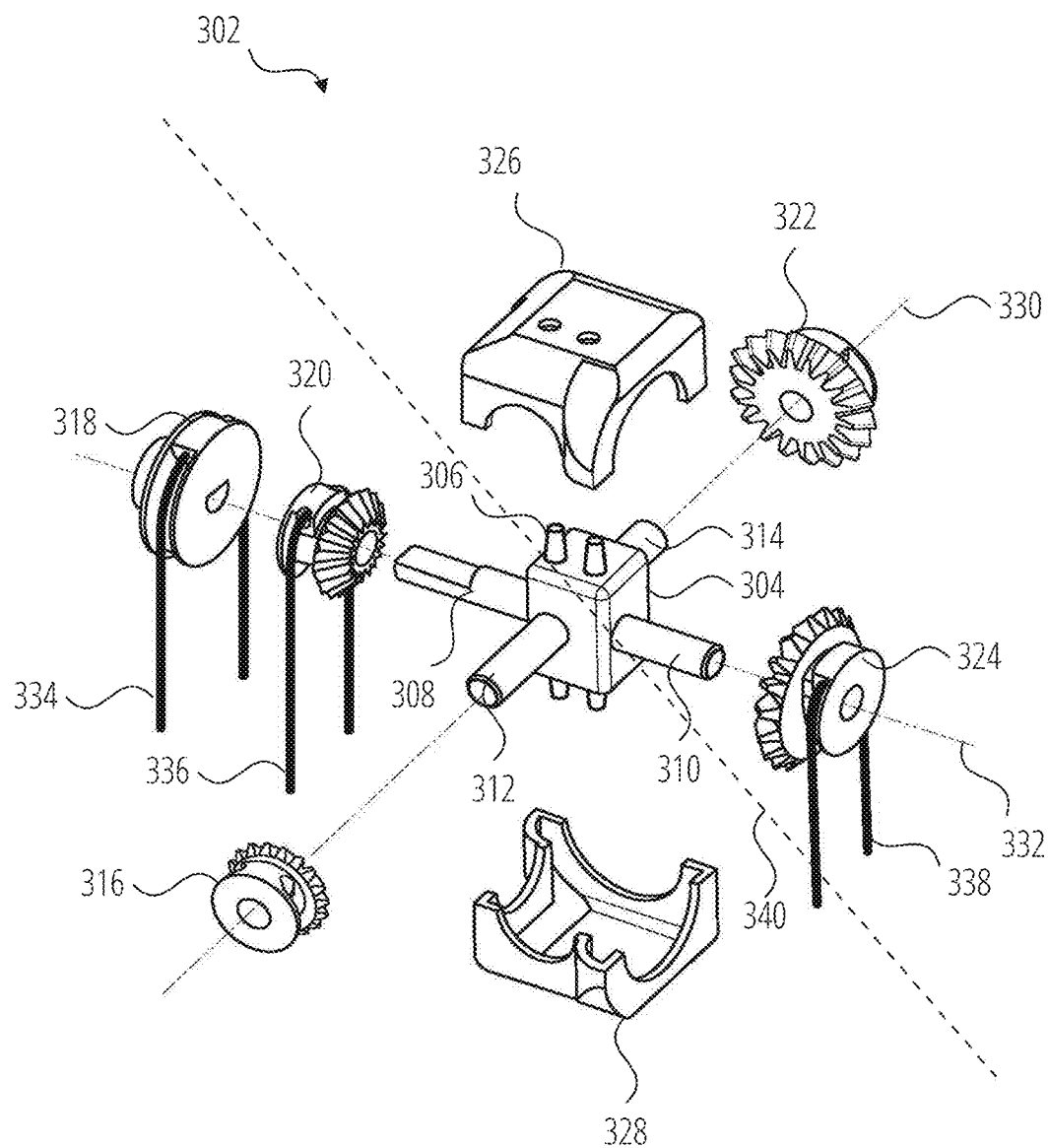
FIG. 3 illustrates an exploded view of an asymmetric gear assembly in accordance with an embodiment.

FIG. 3 depicts an exploded view of a schematic design of an asymmetric gear set and housing of one example in accordance with certain embodiments of the present disclosure. In an embodiment, the asymmetric gear set may have a first drive gear 320 and a first actuator gear 316 making a first gear set. The individual gear of the first gear set may have a common shape and common physical properties, so the two gears mesh well together. Similarly, the second drive gear 324 and second actuator gear 322 may form the second gear set. The individual gears of the second gear set may have a common shape and physical properties, so the two gears mesh well together.

In an embodiment, a block 304 forms the center of a joint, the block 304 having the first prong 308, second prong 310, third prong 312 and fourth prong 314 extending from the block 304. The first prong 308 and second prong 310 may line up on opposite sides of the block 304 and define a first axis 332. The third prong 312 and fourth prong 314 may line up on opposite sides of the block and define a second axis 330. In the various embodiments, one or more guide pin 306 may protrude through, or fit into a recess of a housing to secure the position of the housing to the block 304 and reduce the amount of play between the housing and any interior components. In various embodiments, the block and housing combine to form a mechanical limit on the axial play of each gear as it rotates on a prong. The mechanical limit to reduce axial play may be made using a variety of physical components in a large variety of combinations. In an embodiment, the block may be replaced with flange, washer, or other element that prevents the gear from tilting or sliding axially toward the center of the joint. In another embodiment, the housing may be replaced with an end cap on each prong, a lock pin, a washer or nut, or other element that may prevent the gear from tilting or sliding axially away from the center of the joint. Use of any combination of these or equivalent functional pieces may form the restraint mechanism.

In the various embodiments, the first gear set may have different physical parameters from the second gear set, making the first gear set either smaller or larger than the second gear set. The asymmetry may extend to more than physical dimensions. The first gear set may be made of different materials than the second gear set, so the two gear sets may transmit comparable amounts of torque or mechanical work while being physically different in size and/or shape. In the various embodiments, the first drive cable 336 and the second drive cable 338 may be made of similar material, and have similar structural and physical properties, such as being able to exert similar forces on the respective gears. In some embodiments, the cable for the gear that has the smaller physical dimension, may also be a smaller gauge cable, but able to perform the same level of mechanical work as a larger gauge cable associated with a larger drive gear. This may be achieved by using a higher grade cable for the smaller cable, and a lower grade cable for the larger cable. In some embodiments, the cables for the first drive gear 320 and second drive gear 324 may be the same. In some embodiments, the cables for the first drive gear 320 and the second drive gear 324 may be different.

In some embodiments, the asymmetric gear sets are positioned on the joint (block and prongs) so the first gear set may be mechanically engaged together, and the second gear set may be mechanically engaged together, while the first and second gear sets do not interfere with each other. The prongs for the first drive gear 320 and the first actuator gear 316 may be arranged for the gears to be closer than the second drive gear 324 and second actuator gear 322, allowing the four gears to rotate on their respective prongs without interfering with each other. In an embodiment, the first axis 332 and the second axis 330 may be substantially orthogonal to each other. By substantially, it is meant that the relationship between the prongs defining the axis may be +/−15 degrees from orthogonal. In this way, it may be possible to line up the axis so the first gear set (the smaller gear set in this non-limiting example) so they are closer together, while the second gear set may be farther apart, allowing the second gear set to be larger.

The first gear set and the second gear set may be asymmetric to each other when viewed about a third axis 340 between the first axis 332 and the second axis 330. The axis 340 may be defined as a center line separating the first and second gear sets such that the axis 340 is equidistant from both the first and second gear sets along its length. In some examples, the axis 340 may be defined as a perpendicular bisector of a line segment that connects the first and second gear sets. In some examples, the axis 340 may be defined as a line that extends in a direction halfway between the first axis 332 and the second axis 330. In some examples, the axis 340 is a diagonal axis when it extends diagonally between the first axis 332 and the second axis 330, where the third axis 340 lies on the same plane that is defined by the first axis 332 and the second axis 330. In some examples, the third axis 340 is between the first axis 332 and the second axis 330, where the third axis 340 and the first axis 332 form an angle with a degree greater than 0, and the third axis 340 and the second axis 330 form an angle with a degree greater than 0. In some embodiments, the third axis 340 is a diagonal axis having an angle with the first axis 332 equal to an angle with the second axis 330, where the three axes are in the same plane. In some examples, the asymmetry is due to the size and/or shape difference between the two gear sets. In some examples, the size difference is defined by the difference between the diameters of the corresponding gears. In some examples, the shape difference is defined by the difference between the numbers of teeth in the corresponding gears. In some examples, the size and shape differences are geometrically determined based on at least one physical dimension of the corresponding gears.

In some embodiments, a housing may be used to constrain or confine the first and second gear sets onto their respective prongs, so the individual gears have the minimum play practical on their respective prongs. The housing may have an upper housing 326 and a lower housing 328, which may be assembled over the asymmetric gear set. In various embodiments, the housing may have an asymmetric design to accommodate the asymmetric gears. The housing may have expanded grooves or protrusions for housing the larger gear set, and a smaller configuration to go over the smaller gear set. In various embodiments, the upper housing 326 and lower housing 328 may have cut outs that form apertures in the assembled housing. The apertures may allow a drive portion of the first drive gear 320 and second drive gear 324 to protrude outside the boundary of the housing, and each receive a respective drive cable. In these embodiments, the drive cables may rotate the drive portion, and drive the drive gears, while the gears are secured inside the housing and allowed to rotate, but not slide axially on their prongs. Similarly, the first actuator gear 316 and second actuator gear 322 may have connector portions to actuators, tools, sensors or other elements that may be moved while outside the housing (these elements are omitted from this figure for clarity).

In some embodiments, a wrist gear or wrist driver 318 may be seated on the first prong 308. The first drive gear 320 may be seated on the first prong 308 closest to the block 304, then constrained axially between the upper housing 326 and lower housing 328 assembly and the block 304. The wrist driver 318 may then be fixed to the first prong 308 in a manner that rotation of the wrist driver 318 causes the joint and asymmetric gear assembly 302 to rotate on the first axis 332. The wrist driver 318 may be secured to the first prong 308 using a fastener, solder, glue, interference fit or any other suitable method of securing the wrist driver 318 to the first prong 308. The wrist driver 318 may have a wrist cable 334 attached to it.

In the various embodiments, the various gears of the asymmetric gear joint may be made from a variety of suitable materials. Surgical instruments may be made from metals such as stainless steel, titanium, tantalum, platinum and palladium. Various alloys are also suitable for use in surgical tools, and for the materials of the actuators, gears, housing, cables and other parts of the surgical tool and asymmetric gear joint. In other embodiments, polymers may be used for one or more components, up to and including all components of the surgical tool, the pulley housing, shaft and asymmetric gear joint.

In various embodiments, the different sizing of the first drive gear and the first actuator gear (the first gear pair) may call for using materials with higher strength, greater durability, higher Youngs modulus, and overall improved performance factors and/or traits over the material used for the second drive gear and the second actuator gear (the second gear pair). In some embodiments, the first gear pair may be smaller in at least one physical dimension than the second gear pair. For example, the first gear pair may be smaller in diameter or height, versus the second gear pair. In an embodiment, the smaller first gear pair may be made from higher strength material than the second gear pair, so that the amount of torque, force or other mechanical strain placed on the smaller first gear pair, may be equivalent to the amount of strain of that the second gear pair may experience under load.

In some embodiments, the second gear pair may have smaller physical dimensions than the first gear pair, in which case the compensation of the strain and torque the second gear pair may endure may be greater than the first gear pair.

In some embodiments, one or more components of the device described herein may be made of a polymer, such as biocompatible polypropylene, polycarbonate, polyetheretherketone (PEEK), or other suitable polymers. In some embodiments, one or more components of the device described herein may be made from a ceramic or ceramic composite, ceramic alloy, or ceramic polymer. In some embodiments, one or more components may be made from a nanocomposite material.

In some embodiments, the various gears may be made using one or more of MIM, CNC, EDM or other suitable machining/molding processes. The actuators may be made using similar techniques with CNC used for post operations (such as clearing burrs or flash, polishing and so on). The gear housing may be made from plastic injection molded materials, or MIM if the housing may be made of aluminum, stainless steel or other metals/alloys. The housing halves may be joined after assembly of the asymmetric gears and joint/cross bar by using ultrasonic welding (plastic), laser welding (metal) or adhesives (any material). Grease or other lubricant may be put into the housing to help the gears rotate with less friction. The grease may be added prior to the housing being assembled, or after.

Figure 4:
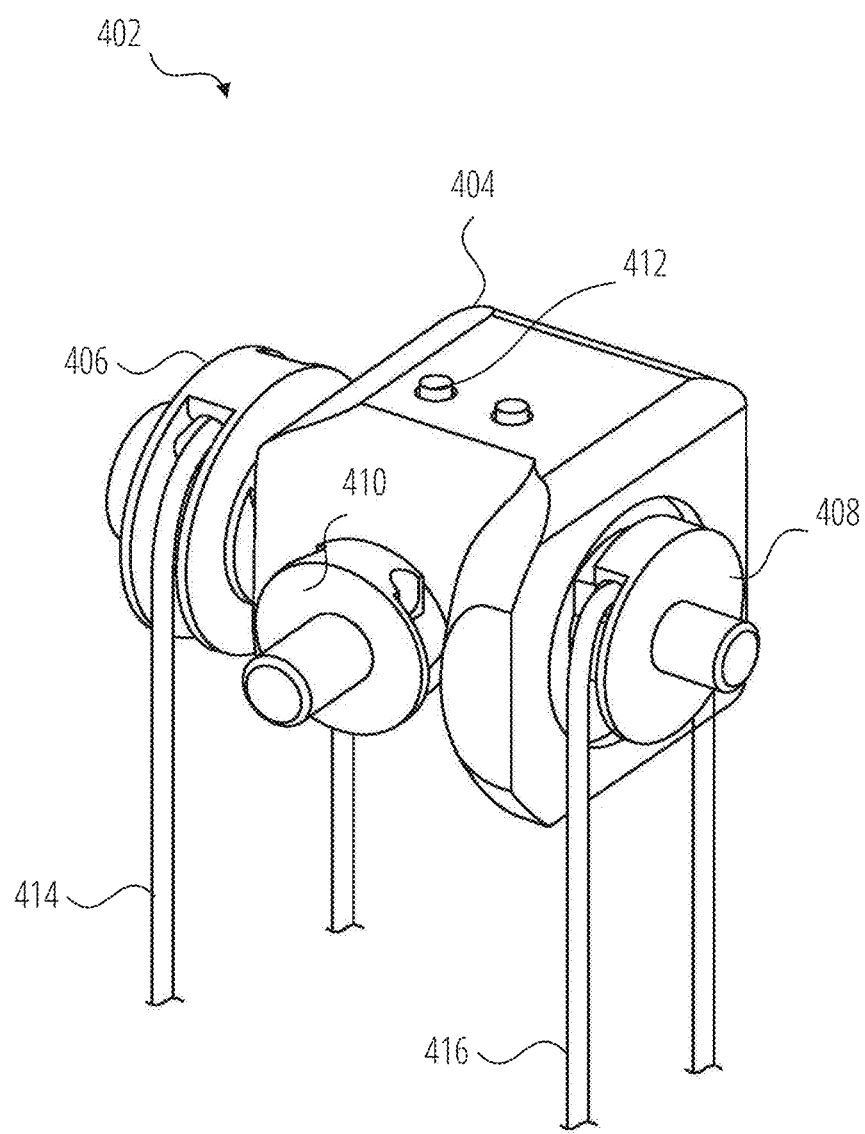
FIG. 4 illustrates an assembled view of the asymmetric gear assembly in accordance with an embodiment.

FIG. 4 depicts one example of a schematic design of the assembled asymmetric joint 402 in accordance with certain embodiments of the present disclosure. In an embodiment, the assembled housing 404 encloses the asymmetric gears. The drive portion of the second drive gear 408 with the second drive cable 416 may be seen extending from one face of the housing 404. The first drive gear remains mostly obscured in this figure. The wrist gear 406 may be viewed as being outside the housing 404, and on the same axis as the second drive gear 408. The wrist gear 406 (or wrist driver, as the terms may be interchangeable as used herein), may have a wrist cable 414. In the various embodiments, one or more guide pin 412 may protrude through, or fit into a recess of (not shown), the housing 404 to secure the position of the housing 404 to the block and reduce the amount of play between the housing and any interior components. The first actuator gear 410 may be partially viewed, as the gear portion remains inside the housing 404 while the portion that connects to the first actuator may be seen. The actuator is omitted for clarity in this figure.

Figure 5:
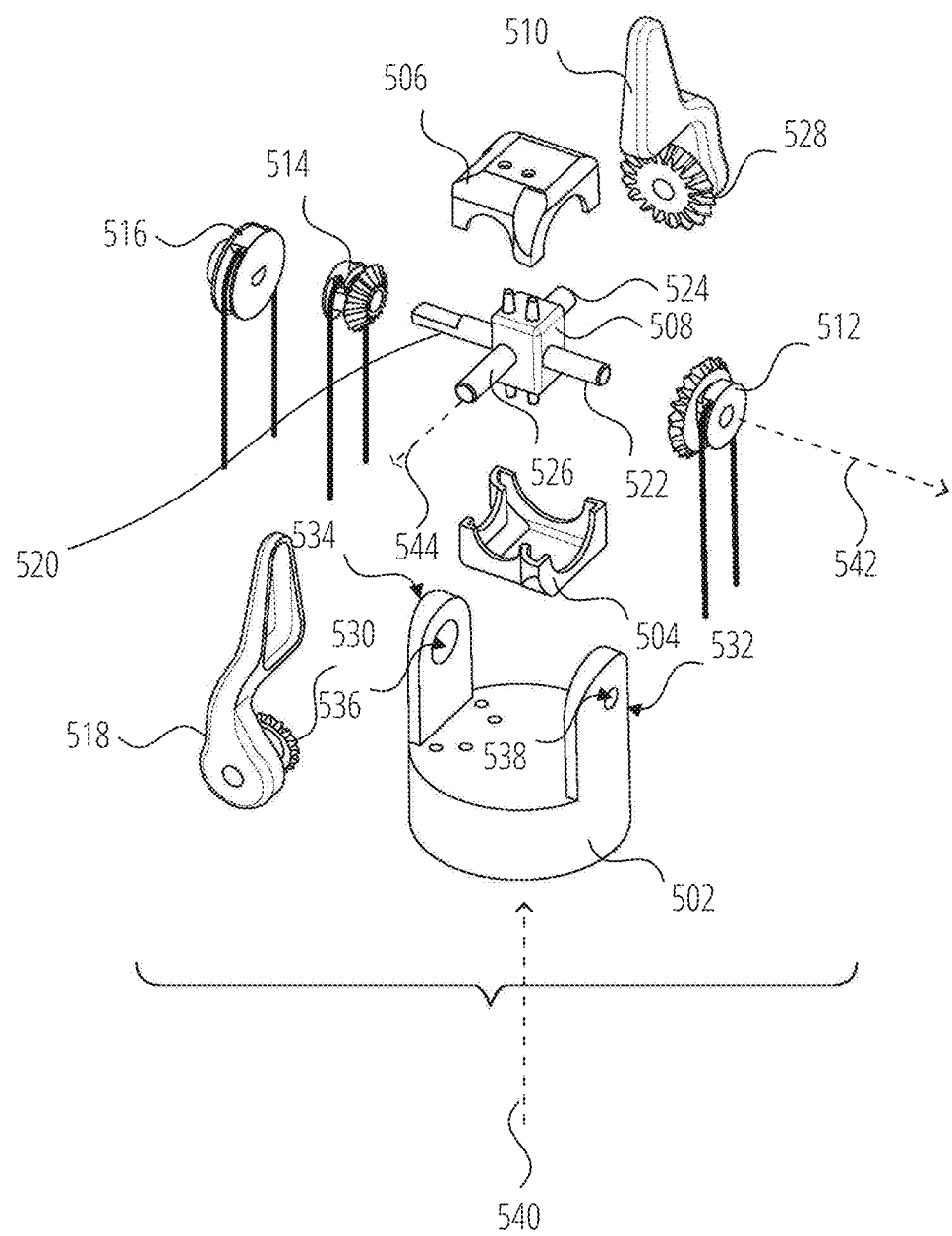
FIG. 5 illustrates an exploded view of the surgical instrument in accordance with an embodiment.

FIG. 5 depicts an assembly view of a schematic design of one example of the surgical tool in accordance with certain embodiments of the present disclosure. In the many embodiments, it should be understood that the assignment of terms such as first prong and first drive gear are purely arbitrary and simply assigned for ease of understanding the present disclosure. There is no 'first' or 'second' as far as importance or operation, these are merely terms used differentiate the parts, and to assist in the understanding of the present disclosure. With this understanding in place, the arbitrary assignment of terms used herein are the first drive gear 514, first actuator gear 530, second drive gear 512, second actuator gear 528, first prong 520, second prong 522, third prong 526 and fourth prong 524. In some embodiments, the combination of the block 508 and prongs may for a joint. In an embodiment, a base 502 may have a pair of tabs extending from the base 502. The tabs may support the block 508 by having the first prong 520 and second prong 522 extend through apertures in the tabs. In some embodiments, one or more components may extend from the exterior of the tabs to the interior and make connection with the first and second prongs. The exact form of the creation of the axle which the joint rotates on may be constructed in a variety of ways, as will be apparent to one of skill in the art on review of this description.

In an embodiment, the upper housing 506 and lower housing 504 may form a cage like housing that may hold the block 508, and a gear set. The gear set may have the first drive gear 514, first actuator gear 530, the second drive gear 512 and second actuator gear 528. The block 508 may have the first prong 520 and second prong 522 arranged in an axial alignment, as well as the third prong 526 and fourth prong 524 in another axial alignment, with the two axial alignments substantially orthogonal to each other. The first drive gear 514 and first actuator gear 530 are paired together, with the first drive gear providing rotational motion to drive the first actuator gear. The first drive gear 514 and first actuator gear 530 for the first gear pair. The second drive gear 512 and second actuator gear 528 are paired together and form the second gear pair. The second drive gear 512 provides rotational motion to drive the second actuator gear 528.

In some embodiments, the operation of the first drive gear 514 and second drive gear 512 may move independently. In an embodiment, the first actuator gear 530 may be mechanically engaged to, connected to, or part of, the first actuator. In an embodiment, the second actuator gear 528 may be mechanically engaged to, connect to, or part of, the second actuator 510. Thus, in operation, the first and second actuators may be moved in synchronous motion together, or may work individually to achieve cooperative functions, such as grasping, moving, pushing and so on.

In various embodiments, the first drive gear 514 and second drive gear 512 may have a gear portion and a drive portion. The gear portion may be a beveled gear, or other gear shape that allows the transfer of mechanical force from the drive gear to the actuator gear when the two gears are positioned in a generally orthogonal position to each other. The drive portion of each gear may have a substantially circular recess for receiving a cable. The cable may be attached to the drive portion. In some embodiments, the cable may be crimped, soldered, glued or in some way fastened to the drive portion of the gear. The gear portion may rotate on a prong, and the gear portion may be larger than the drive portion, such that there may be a step down in size from the gear portion of the drive gears, and the drive portion of the drive gears. In this manner, the drive gears may have the gear portions inside the housing, while the drive portions extend through appropriately sized apertures in the housing. In various embodiments, this allows drive cables to be mechanically engaged with the drive gears, while the gear portions of the drive gears are held in a rotational alignment with the prong the gear may be rotating around.

In some embodiments, the first actuator gear 530 and the second actuator gear 528 may have a similar design such that the gear components of the actuator gears may be held inside the housing, while a neck or step portion of the first and second actuator gear may extend through an appropriately sized aperture in the housing. In this manner the first and second gear pair may be held in place with each gear on their appropriate prong, and confined to a rotational position such that the gears may not become misaligned or disconnected, so that mechanical force may not be lost when the drive gears are actuated.

In an embodiment, the first prong 520 may be longer than the other prongs, so the first prong 520 may extend through the first drive gear 514, and the wrist driver 516. The shape of the first prong 520 may be changed so that the first prong engages with the wrist driver 516 in a manner that may not allow the wrist driver to rotate relative to the first prong 520. In this way, when the wrist driver 516 is actuated by a cable or other drive means, the first prong 520 and the entire block 508 and housing assembly may rotate on the axis defined by the first and second prongs.

In some embodiments, the block 508 may have additional pins or tabs extending from the block 508. The pins or tabs may align with apertures in the upper housing 506 and lower housing 504, to keep the block 508 in a fixed position within the housing after the housing may be assembled.

In another embodiment, there may be a minimally invasive surgical tool with six degrees of freedom and a single wrist. The surgical tool may have a base 502, with a first tab 534 and second tab 532 extending distally (away from the base and pulley housing). The first tab 534 and the second tab 532 may be arranged to contain or receive an axle. The base may be rotatable about a first axis 540. The surgical tool may have a joint having a first pair of prongs aligned in a second axis 542 to form the axle on either side of the joint. The first pair of prongs may be mechanically engaged to the pair of tabs, and rotatable in the first prong aperture 536 and the second prong aperture 538. The joint may have a second pair of prongs aligned in a third axis 544, the second pair of prongs being substantially orthogonal to the first pair or prongs. In an embodiment, a housing may be fittingly engaged to the joint, such that the first pair or prongs and the second pair of prongs protrude from the housing when the joint may be placed within the housing. A first drive gear 514 may be positioned on a first prong 520 of the first pair of prongs. The first drive gear 514 having a first diameter. A second drive gear 512 may be positioned on a second prong 522 of the first pair of prongs. The second drive gear 512 may have a second diameter, where the first diameter may be different from the second diameter. In an embodiment there may be a first actuator gear 530 positioned on the first prong of the second pair of prongs. The first prong of the second pair of prongs may coincide with the third prong 526. The first actuator gear 530 may have a diameter that may be the same as the first drive gear 514. A second actuator gear 528 may be positioned on the second prong of the second pair of prongs. The second prong of the second pair or prongs may coincide with the fourth prong 524. The second actuator gear 528 may have the same diameter as the second drive gear 512. A first actuator 518 may be fixedly attached to the first actuator gear 530, the first actuator 518 may be rotatable in response to movement of the first actuator gear 530. A second actuator 510 may be fixedly attached to the second actuator gear 528, the second actuator 510 may be rotatable in response to movement of the second actuator gear 528. The first and second actuators may be movable in six degrees of freedom by rotating the first and second actuators about the first, second or third axis.

In some embodiments, the gears may be integrated into the actuators and the gear plus actuator may be manufactured as a single unit. The gear may be integrated into the fabrication of the actuator, machined as part of the actuator, or otherwise created in any fashion as may be understood in the art.

In an embodiment, the actuators may be moved independently from each other. The actuators may move cooperatively in the same direction, or one may move while the other is stationary relative to the base. In some embodiments, each actuator may move in opposite directions, same directions, at the same or different speeds. In the many embodiments, the use of actuator should not be taken as limiting in any sense. The first and second actuator gears may drive any tool, sensor, instrument, probe or device that may be suitable for attachment to the actuator gears. The actuators may be used to grasp, tear, probe, scan, cut, retract, dilate or remove tissue, foreign objects from the body or any other material the surgical tool may be adapted to handle. In some embodiments, cooperative actuators may act as tweezers, graspers, scissors, clamps, forceps, and so on. In some embodiments, opposition actuators may act as dilators, retractors, tissue cutters and so on.

In various embodiments, the materials and construction techniques may be any known in the art, as well as those described herein. In an embodiment, the base 502 may be made using MIM with post-operations with CNC machining, or made entirely using CNC machining. The block 508 and prongs may form a single unit, which may be referred to as the joint or the cross base. The joint may be made using MIM and/or CNC processes. The individual prongs may be CNC machined, or the prongs may be welded or secured to the block. In some embodiments one set of prongs may be a continuous rod that may extend through the block. In an embodiment, the cable elements may be braided and crimped to the neutral position of the individual gears and/or pulleys. The cables may also be secured by welding, adhesive or other bonding techniques. In some embodiments, the surgical tool may be disposable, so the materials and fabrication techniques may be of different quality than if the surgical too may be reusable. A disposable tool may not need the same useful life and duration as a reusable tool.

Figure 6:
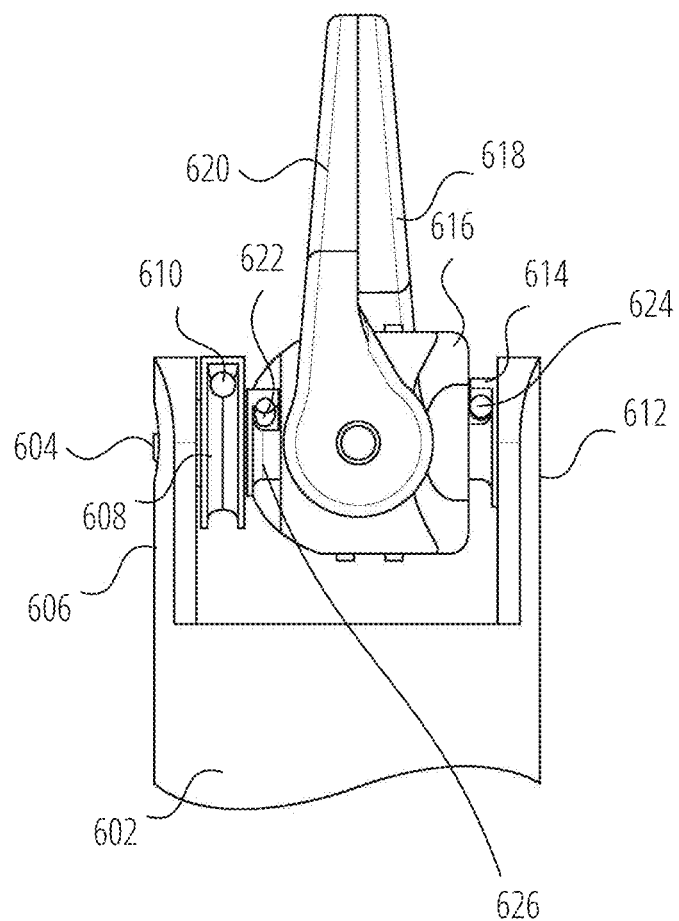
FIG. 6 illustrates a side view of the surgical instrument according to an embodiment.

FIG. 6 depicts a side view of a schematic design of one example of the surgical instrument in accordance with certain embodiments of the present disclosure. In an embodiment, the base 602 of the surgical instrument supports a pair of brackets 606, 612. A prong 604 or rod may extend through the bracket 606. In some embodiments, the bracket may not have an aperture through the bracket, but instead have a socket, indentation or other mechanical receiver for the prong or rod, permitting the side of the bracket 612 to be smooth. In some embodiments, there may be joint with four (4) prongs (or rods) extending there from. The prongs may form a first and second axle, with the prongs arranged in a linear fashion. In some embodiments, the first axle may be formed with the first prong 604. In various embodiments, the first and second drive gears may be disposed within the housing 616. The drive gears may be connected to drive spools or cable carrying elements. A first drive cable 624 may be connected to the first drive gear 614. A wrist drive cable 610 may be connected to a wrist spool 608, while a second drive cable 622 may be connected to the second drive gear 626. The wrist drive cable 610 may provide the force to move the joint contained within the housing 616 around the axis defined by the first prong 604. The first and second drive gears may be connected to the first and second actuator gears (not visible inside the housing) and may be independently controlled. In various embodiments, the actuators (e.g., the first actuator 620 and the second actuator 618) may also be used to grip a body part, another tool, or component needed for a surgical procedure.

Figure 7:
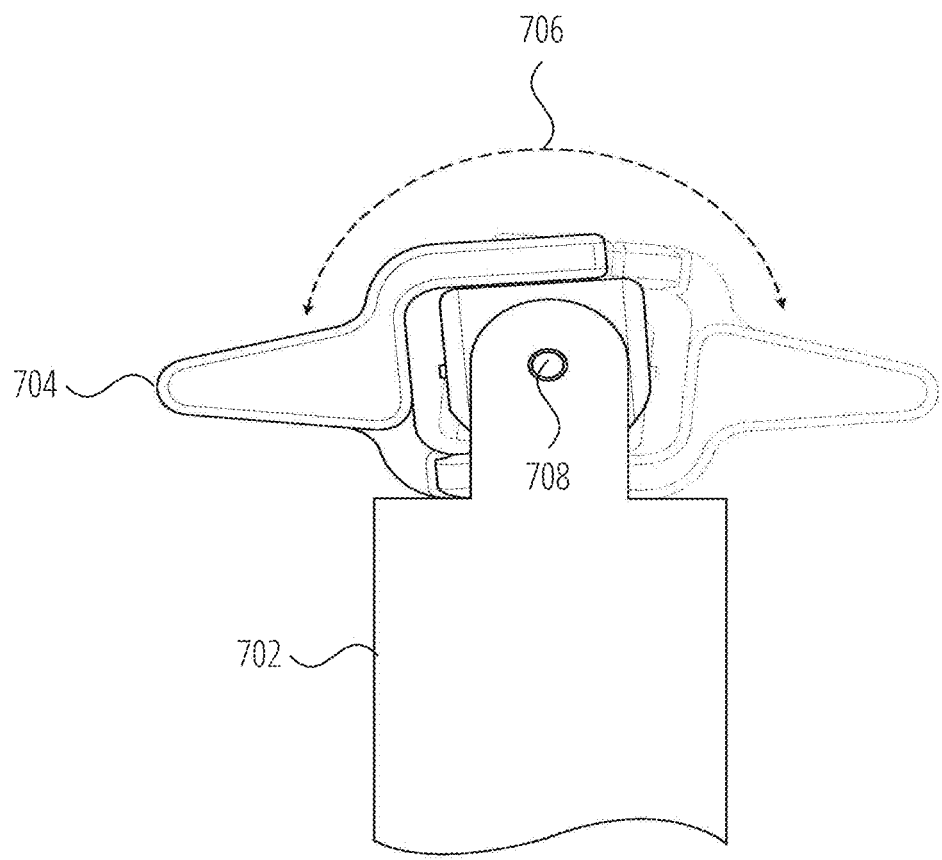
FIG. 7 illustrates a rotation arc of the actuator according to an embodiment.

FIG. 7 depicts a side view of a schematic design of one example of the single wrist surgical instrument in accordance with certain embodiments of the present disclosure. In an embodiment, one or more actuators 704 may rotate around a first axis 708, with a range of motion 706 as indicated by the dotted line. The orientation of the actuator 704 may be adjusted by controlling the rotation of the bases 702 along the axis of the tool, and the actuator motion through the first and second drive gears, the combination allows roll, pitch and yaw control of the actuator elements. In some embodiments, the range of motion 706 may be increased by changing the surface of the base 702 such that the actuators 704 do not come into contact with the base 702 being horizontal. In various embodiments, one or both sides of the base may be sloped up or down to increase or decrease the range of motion 706 in one or both directions. In an embodiment it is not necessary for the slope of the base surface to be uniform on the left and right sides.

Figure 8:
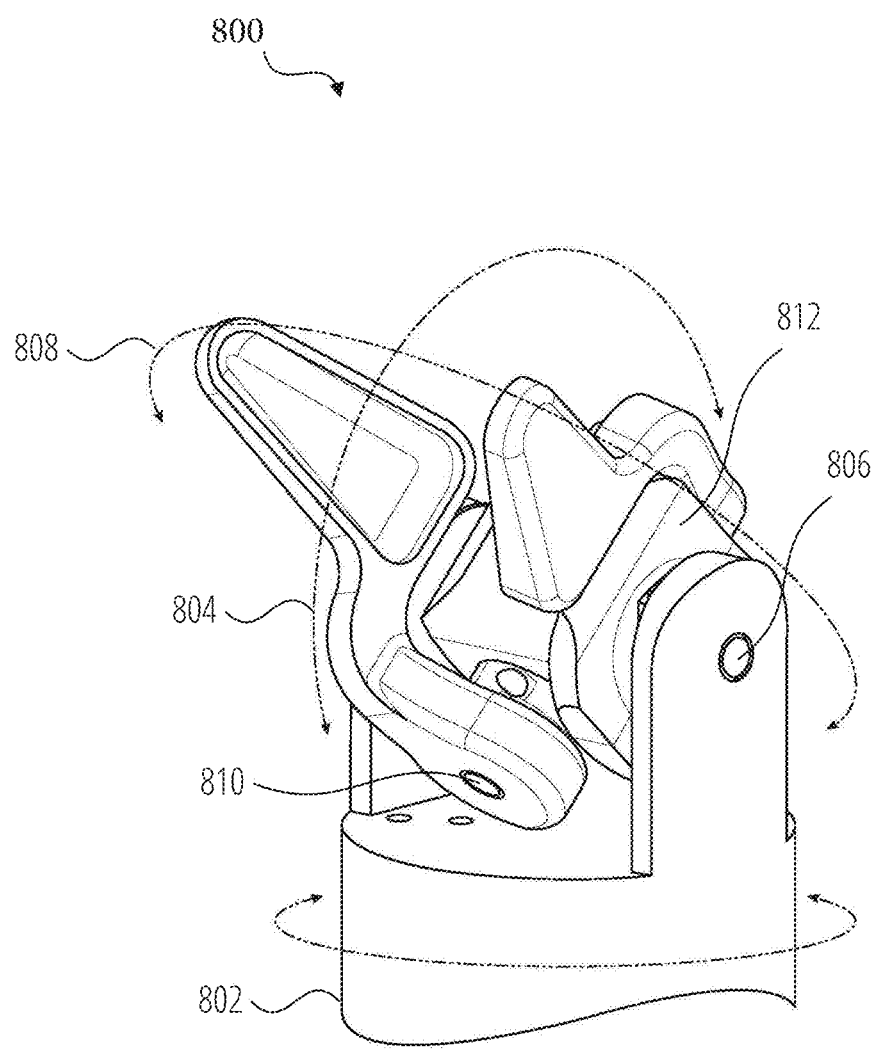
FIG. 8 illustrates possible movement arcs of the surgical instrument according to an embodiment.

FIG. 8 depicts a perspective view of a schematic design of one example of the single wrist surgical instrument 800 in accordance with certain embodiments of the present disclosure. In an embodiment, the base 802 may swivel or rotate on the main axis of the surgical instrument 800. The brackets remain stationary relative to the base 802, and the housing 812 may rotate around the first axis of motion 806 along the first arc of motion 804. The actuators may rotate around the second axis of motion 810 along the second arc of motion 808. As the base 802, and housing are rotated. The actuators may be oriented toward nearly any position in a hemispherical volume about the center position of the joint.

Figure 9:
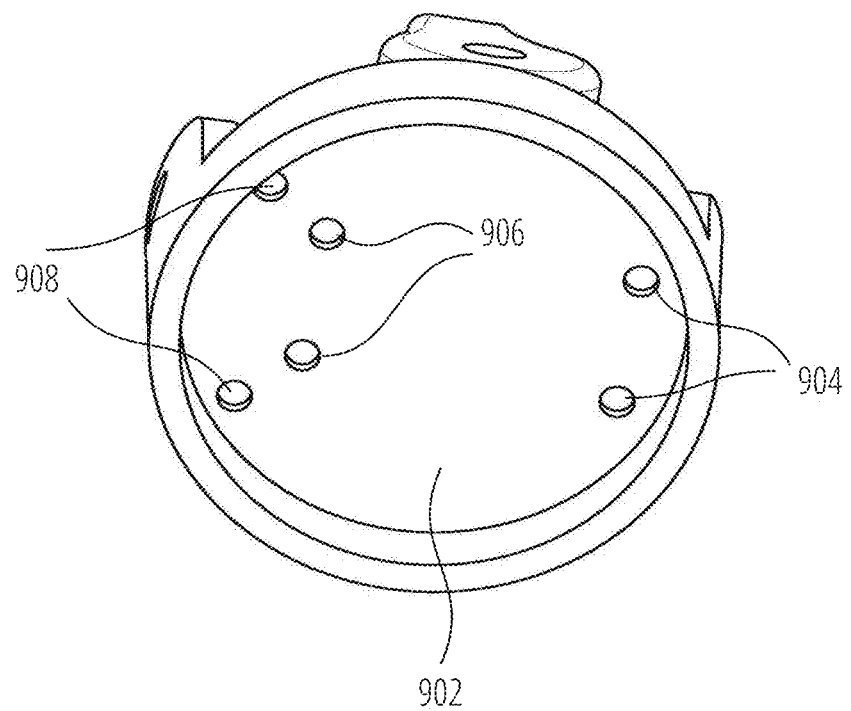
FIG. 9 illustrates the underside view of the surgical instrument base according to an embodiment.

FIG. 9 depicts a bottom view of a schematic design of one example of a base 902 in accordance with certain embodiments of the present disclosure. The base 902 may have a plurality of apertures for cables, or other force transmitting mechanisms to reach from the proximal side of the base, to the distal side of the base. In some embodiments, cables may travel through the first cable apertures 904 from a proximal force generating element, such as a motor, a hand actuated level, a slidable piston, and so on. The cable may wrap around or attach to the first drive gear, or a spool or other connected element that transmits the cable motion to the drive gear. The second cable apertures 906 may allow a cable or other drive element to pass through to the second drive gear, and the wrist cable apertures 908 may permit a cable to pass through to the tertiary drive spool.

The base 902 may rotate on the main axis of a medical instrument distal end, such as on the distal end of a robotic arm, robotic accessory or manually controlled medical tool.

Figure 10:
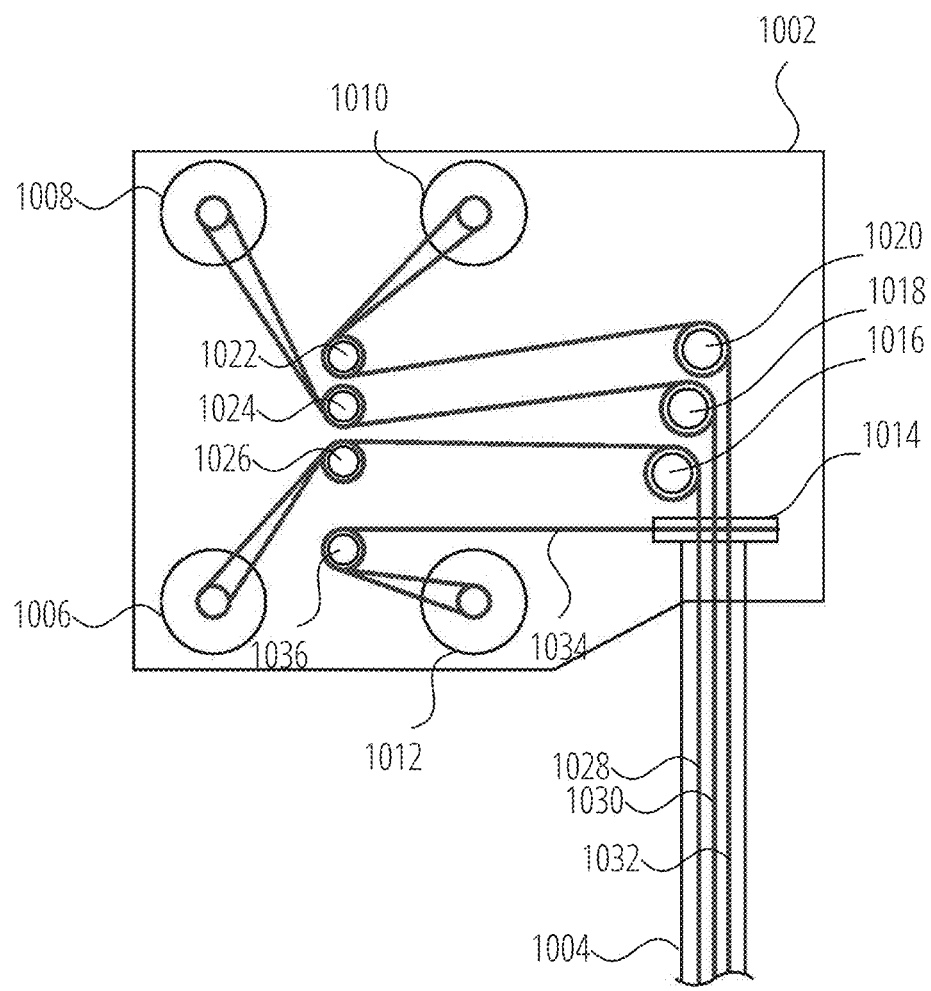
FIG. 10 illustrates a pulley housing assembly in accordance with an embodiment.

FIG. 10 depicts a schematic view of one example of a pulley housing 1002 in accordance with certain embodiments of the present disclosure. The pulley housing 1002 may contain a group of pulleys to transfer motor force through a group of cables that may be connected to the various gears of the gear set. In an embodiment, a shaft 1004 may be connected to, an extension of the base of the surgical tool. The shaft 1004 may be rotated around its axis by a shaft cable 1034 which may connect the shaft collar 1014 and the shaft pulley 1012. In some embodiments, the shaft cable 1034 may be routed around a shaft idler pulley 1036. The shaft pulley 1012 may be driven by a motor outside the pulley housing 1002. The motors may be placed outside the pulley housing 1002 to prevent contamination of the motors from biological particles that may contaminate the various cables. The pulley housing 1002 may be made to be disposable.

In an embodiment, a first drive gear pulley 1006 may drive a first drive cable 1028 around a first drive idler pulley 1026 and a first drive idler pulley 1016 so that the first drive cable 1028 may enter into the shaft 1004 without sliding against the shaft collar 1014. The first drive cable 1028 may be wound around the first drive gear pulley 1006 in two directions, so the first drive cable may extend from the first drive gear pulley 1006, around one or more idler pulleys, through the shaft 1004 to the first drive gear, and return to the first drive gear pulley 1006. The first drive cable 1028 may be a continuous loop, or it may be a single cable with both ends secured to the first drive gear pulley 1006. In an embodiment, the first drive cable 1028 may be two cables, both extending from the first drive gear pulley and ending at the first drive gear.

In an embodiment, a second drive gear pulley 1008 may drive a second drive cable 1030 around a second drive idler pulley 1024 and a second drive idler pulley 1018. The position of the idler pulleys may assist in preventing the second drive cable from getting tangled or sliding against the shaft collar 1014. The second drive cable 1030 may be a continuous cable (loop), a single cable with two ends secured to the second drive gear pulley 1008 or two individual cables, as described for the first drive cable 1028.

In an embodiment, the wrist pulley 1010 may drive a wrist cable 1032 around a wrist idler pulley 1022 and a wrist idler pulley 1020 such that the wrist cable 1032 may enter the shaft 1004 without sliding against the shaft collar 1014. Similar to the cables for the first and second drive cables, the wrist cable may be a continuous loops, a single cable with ends secured on the wrist pulley 1010, or a pair of cables, with each end of each cable secured on the wrist pulley and the wrist gear.

In various embodiments, the position of the drive pulleys and idler pulleys may be adjusted and optimized for various operations and systems. Some devices, such as a robotic surgical system, may have an array of motors available to drive the pulleys, and require the pulleys to be positioned in different configurations to match the robotic surgical system. In some other devices, the pulleys may be operated by hand, as when the surgical tool or the asymmetric joint may be used with a handheld tool.

In various embodiments, the pulleys may be made using CNC machine processes and materials. The pulley housing may be made of a polymer. The pulley housing may be injection molded and then assembled using other parts of the pulley housing. In some embodiments, the pulley housing may be made from two or more pieces, which may be bonded together to form the pulley housing. The pulley housing may also be fastened together using mechanical fasteners such as screws, pins, clamps and so on.

Figure 11:
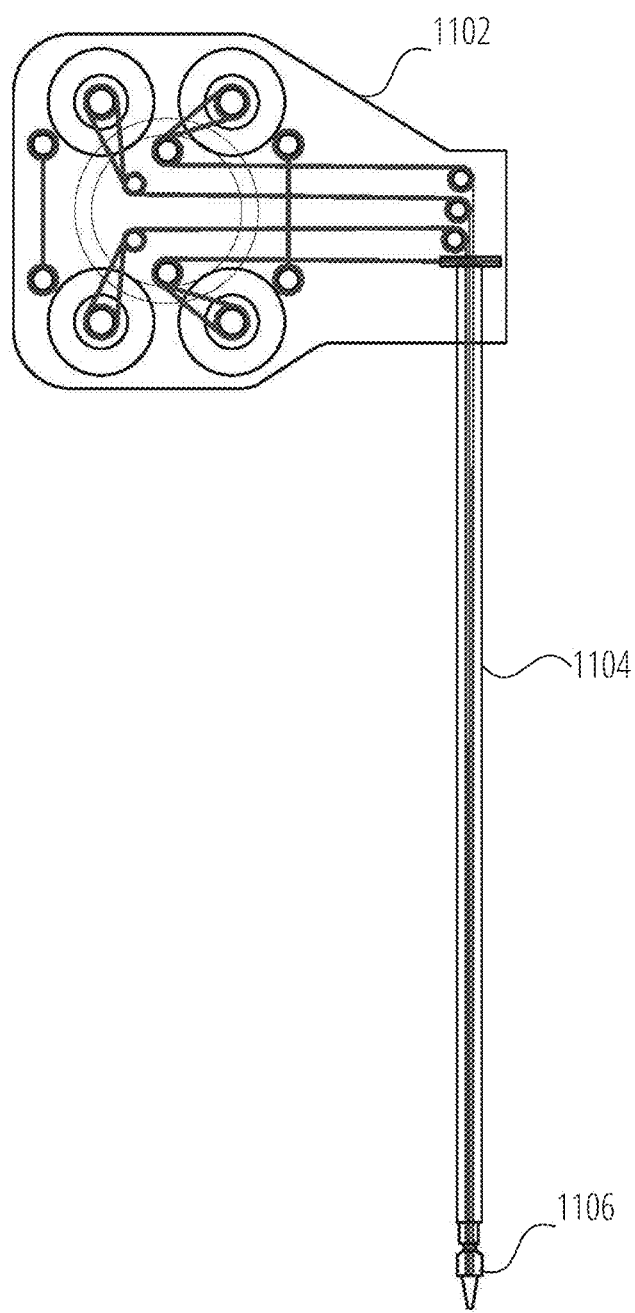
FIG. 11 illustrates a view of the surgical tool, shaft and pulley housing in accordance with an embodiment.

FIG. 11 depicts a schematic view of one example of a pulley housing 1102 in accordance with certain embodiments of the present disclosure. The pulley housing 1102 may be seen in a complete structure with the shaft 1104 and the surgical tool 1106 at the distal end of the shaft 1104. The shaft 1104 may be any length, as may be suitable for the tool or system adapted to use the surgical tool 1106. The shaft 1104 may rotate along with the base of the surgical tool, or the shaft may be stationary while the shaft cable may drive a separate mechanism to cause the rotation of the base of the surgical tool 1106.

Figure 12:
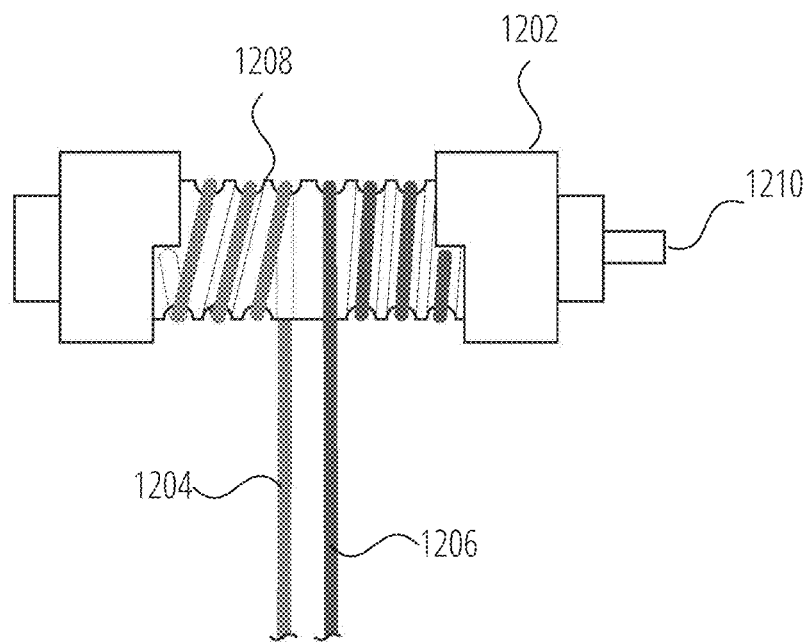
FIG. 12 illustrates a pulley with a drive cable according to an embodiment.

FIG. 12 depicts a schematic view of one example of a drive pulley 1202 in accordance with certain embodiments of the present disclosure. The drive pulley 1202 may be used to transfer rotational force from the motor to a drive gear. The drive gear may be the first drive gear, second drive gear, wrist gear or shaft collar (generally referred to herein as a drive gear, even though the wrist gear and shaft collar may not have a gear component on them). The drive pulley 1202 may rotate on a drive pulley axle 1210, causing the drive cable to simultaneously wind and unwind on the pulley. As the drive pulley rotates in one direction, part of the cable unwinds in the cable out 1206 direction, while the other side is taken in the cable in 1204 direction, and winds around the drive pulley. When the rotational direction may be reversed, the cable unwind side becomes the winding side, and the cable winding side becomes the unwinding side. The drive pulley may have a series or continuous pulley cable recess 1208, for taking up and releasing the cable as it may be wound and unwound. The pulley cable recess 1208 as shown is not the only design of the cable recess for use on the drive pulley, but is merely illustrative.

Figure 13:
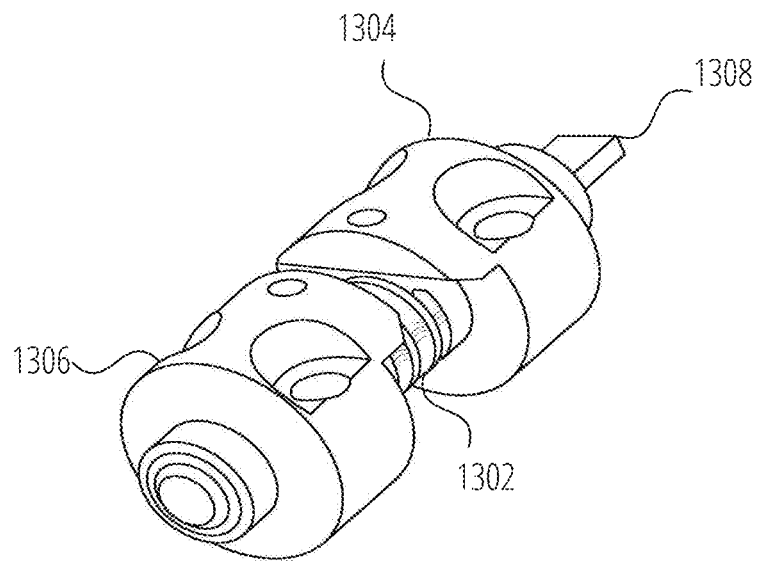
FIG. 13 illustrates a pulley with collars according to an embodiment.

FIG. 13 depicts a schematic view of one example of a drive pulley 1302 in accordance with certain embodiments of the present disclosure. The drive pulley 1302 with a drive tab 1308 for connection to a motor, may have a top collar 1304 and a bottom collar 1306. The top collar 1304 and bottom collar 1306 may fasten the drive cable to the drive pulley 1302. The drive cable is omitted from this view for clarity of the figure. The top and bottom collars may be assembled or fastened to the drive pulley while pinning down and securing the ends of a drive cable, or a designated section of a drive cable. The top and bottom collar may also provide coverage over the drive pulley to protect the drive cable, and keep the cable sorted as the cable may wind or unwind from the drive pulley. Furthermore, it is to be understood that the pulleys may also be referred to as spools when engaging with the cables as described above, that is, when the pulley is configured in the shape of a spool.

Figure 14:
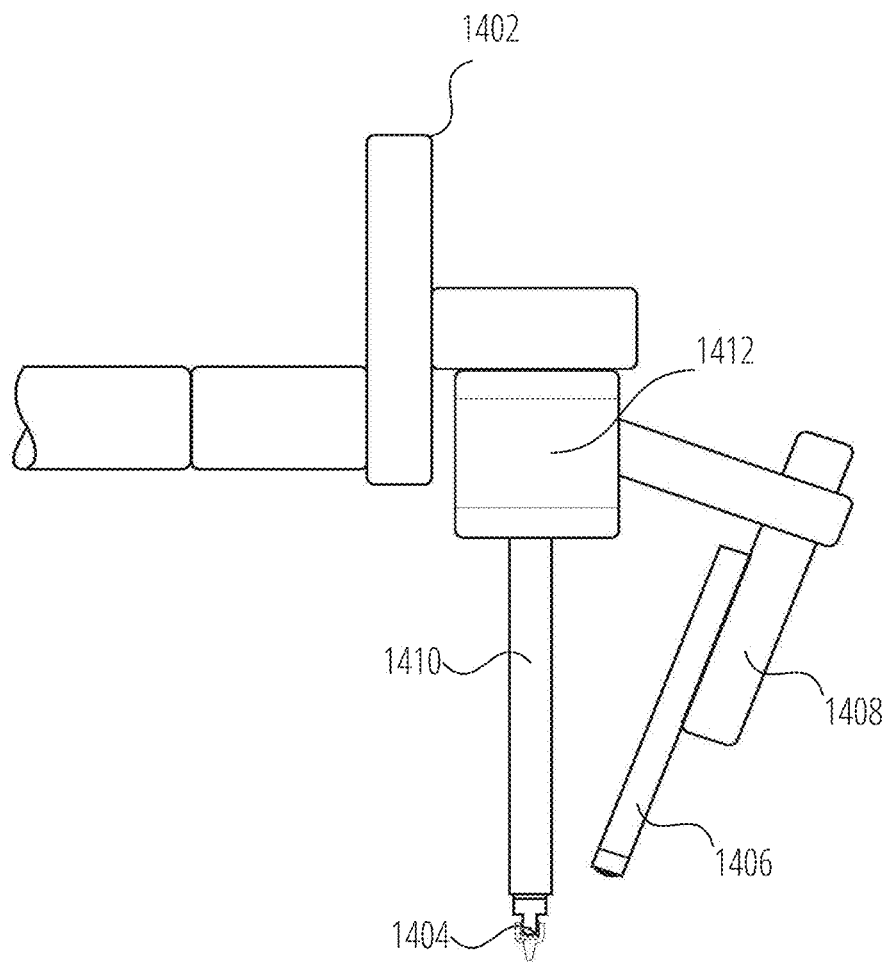
FIG. 14 illustrates a view of the surgical tool on a robotic arm according to an embodiment.

FIG. 14 depicts a schematic view of one example of a surgical tool 1404 in accordance with certain embodiments of the present disclosure. The surgical tool 1404 may be used with a robotic arm 1402. The robotic arm 1402 may have the pulley housing 1412, along with a motor unit and motor controller (not shown), and the shaft 1410. In some embodiments, visualization of a surgical site may be processed through a scope 1406 on a scope arm 1408, and working in conjunction with the surgical tool 1404. A controller may operate the navigation of the surgical tool 1404 while coordinating the motion of the scope 1406 to ensure the tool stays in a visual field of view.

Figure 15:
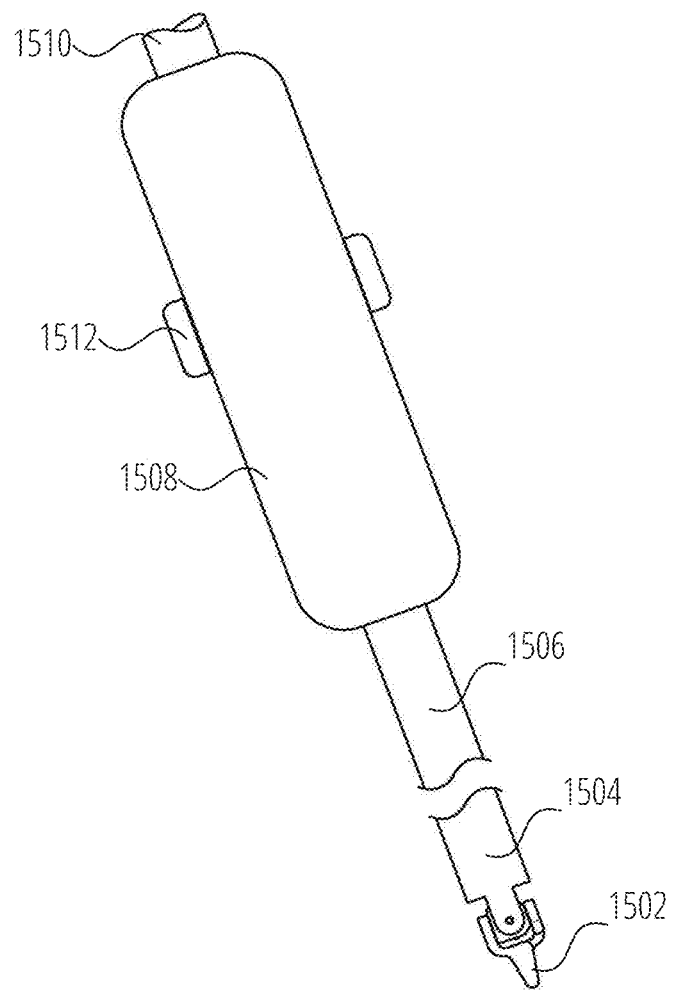
FIG. 15 illustrates a surgical instrument as an end effector of a manually controlled surgical tool in accordance with an embodiment.

FIG. 15 depicts a schematic view of one example of a single wrist instrument 1502 in accordance with certain embodiments of the present disclosure. The single wrist instrument 1502 may be attached to a handheld tool in some examples. In some embodiments, the single wrist instrument 1502 may be connected or attached to the tool distal end 1504. The tool distal end 1504 may have cables or other drive mechanisms connecting the single wrist instrument 1502 to one or more motors or manually actuated drive mechanisms. The tool proximal end 1506 may provide the connection for the single wrist instrument 1502 and the tool handle 1508. The tool may be actuated by a tool control element 1510. In some embodiments, the tool may have additional tool control elements 1512.

In an embodiment, the surgical tool and asymmetric gear assembly may be controlled by a computer. The computer may be an electronic device with one or more processors, one or more types of memory, one or more input/output (I/O) ports to connect to one or more I/O devices, a graphical user interface (GUI), and one or more software programs for controlling and operating the computer. In addition, the computer may have any other such hardware or software components as may be useful in its operation. The computer may be a desktop computer, a laptop, a purpose built computer controller, a mobile device (tablet, PDA, cell phone or other mobile electronic device), or a computer built into or as part of a medical device, such as a robotic surgical device.

Figure 16:
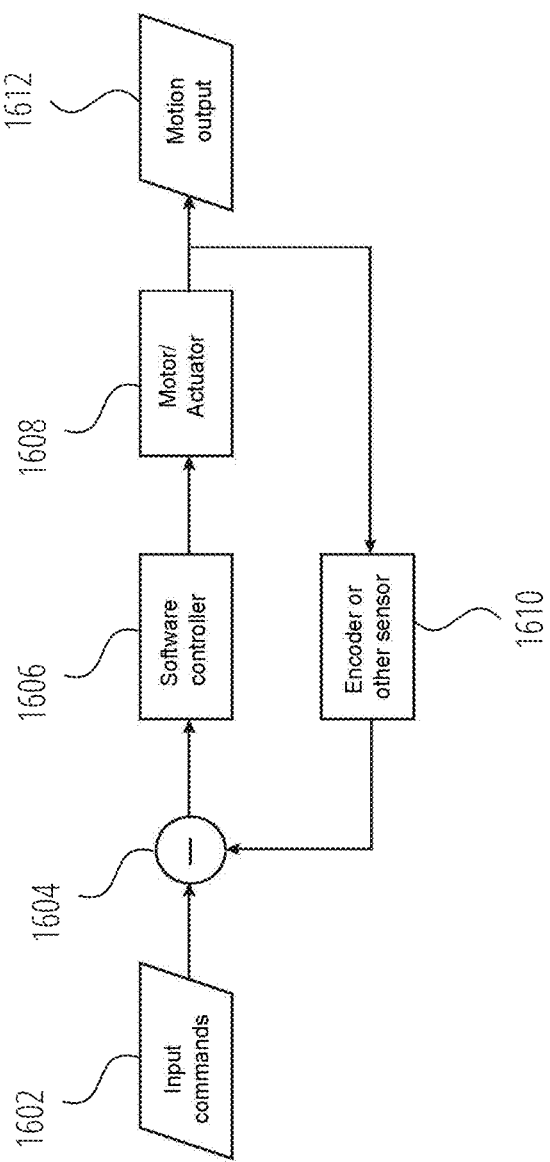
FIG. 16 illustrates a flow chart of a machine controlled motion output for controlling the surgical tool in accordance with an embodiment.

FIG. 16 depicts an example system diagram in accordance with certain embodiments of the present disclosure. The system includes one or more input commands 1602, which may be provided by a user. The user may be a surgeon, technician, or other authorized user of the surgical tool. A computer may handle the electronic communication between the various components with various steps and operations of the computer itself omitted for clarity. The input commands are passed to a software controller 1606 through a negative feedback process 1604. The software controller 1606 may be used to electronically control one or more motors 1608. The motors 1608 may control one or more actuators as described herein. Each motor 1608 and/or actuator may have a sensor or encoder 1610 linked to it, such that any motion or movement of the motor or actuator may be accurately measured. The sensor or encoder 1610 information may be fed into the negative feedback process 1604, so the software controller 1606 may know how much the motor or actuator has actually moved. The output of the motor 1608 and actuators determines the motion output 1612 of the end effectors, which may include actuators, tools, sensors of the like. In some examples, the controller 1606 may be operably coupled with the drive spools or drive pulleys such that the controller 1606 determines the rotation and movement of the gear pairs, for example based on the sizes of the gear pairs, and provide operation control of the drive cables as the motion output 1612 based on the determined rotation of the drive spools. The encoder 1610 may be operably coupled with one or more of the drive spools or drive pulleys.

Robotic surgery systems of various kinds are well known in the field of minimally invasive surgery. Robotic surgical instruments range from a single axis motion, to six or more degrees of freedom, and movement with multiple arms. Some robotic surgery systems are able to control two, three or four robotic devices simultaneously. Robotic surgical devices generally have a mechanical robotic component, a computer, one or more software controllers operating on the computer, and some kind of a user interface that allows a user to direct the movement or operation of the robotic device. In some embodiments, the robotic surgical system may be an autonomous system. A user or set of conditions may provide pre-programmed instructions to the robotic surgery device, and the robotic surgery system engages in the defined procedures independently and autonomously. In some embodiments, the robotic surgery system may be a human guided system with robotic assist. The robotic surgical system may take directions from real time inputs of a user, and the robots motors guide the mechanical elements of the robotic system to the appropriate surgical site. The system may then engage in a variety of functions such as tissue cutting, evacuation of blood and waste tissue, probing and analysis, tissue retraction and so on. In some embodiments when a user may provide direction to the robotic system in real time (or near real time), the robotic system may stop or enter an atraumatic mode in the event a user stops providing input to the robotic controller. In various systems, the robotic surgery system may be automatic, user assisted, or passive. The use of the asymmetric gear assembly and surgical tool may be useful in these three types of robot surgical systems, plus any others now available or future deployed.

Figure 17:
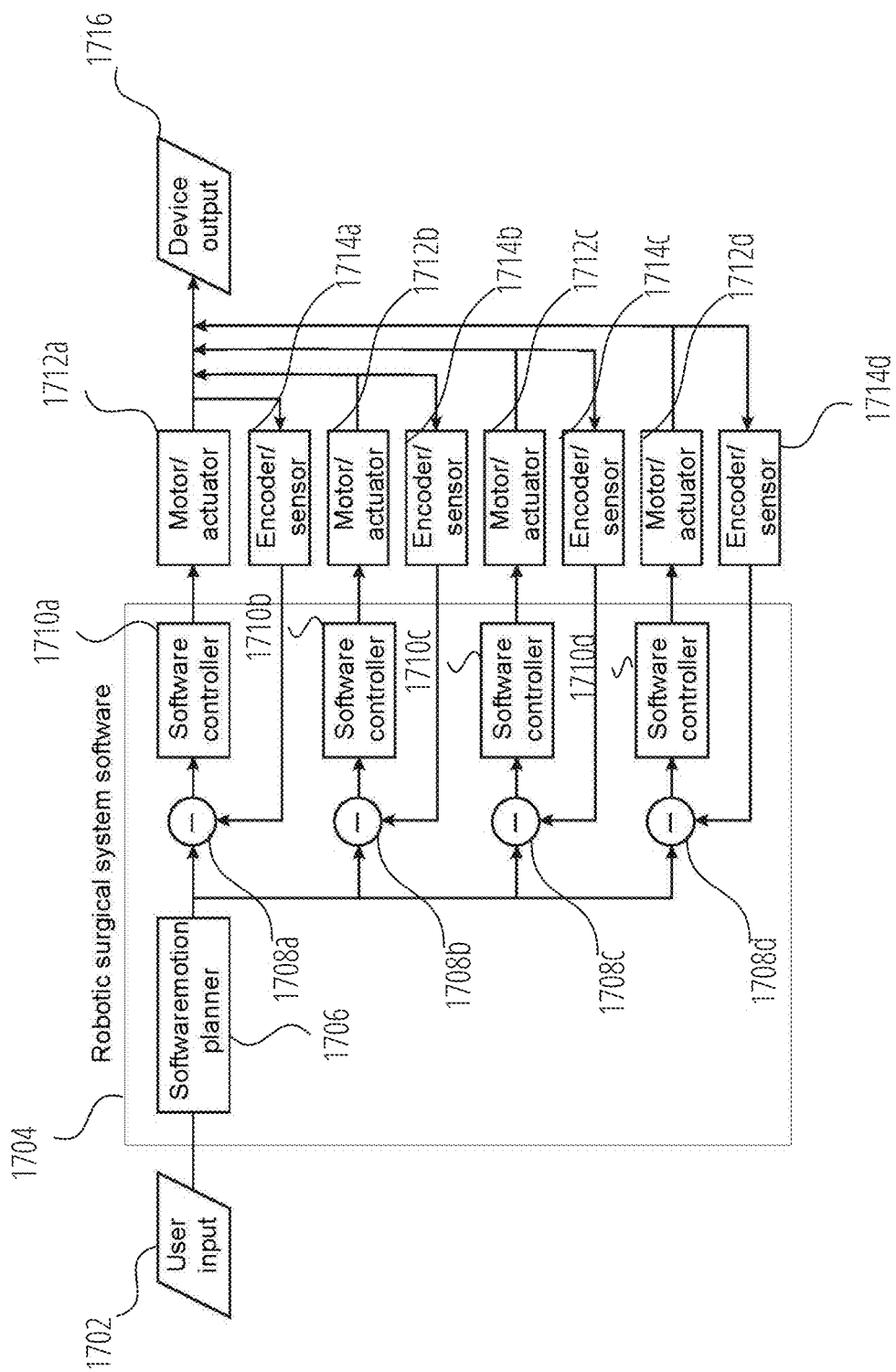
FIG. 17 illustrates a flow chart of a surgical robot and software controller according to an embodiment.

FIG. 17 depicts a flow diagram of one example of a robotic surgery system into which the asymmetric gear assembly, surgical tool, and software controller, may be integrated in accordance with certain embodiments of the present disclosure. The robotic surgery system may have an operating system for controlling the computer, and the robot. The robotic surgery system may have one or more software programs for controlling the asymmetric gear assembly and the surgical tool. The control of the asymmetric gear assembly and surgical tool may be one program, or more than one program that operate simultaneously and in coordination with each other. In an embodiment, the software program for the asymmetric gear assembly and surgical tool may be integrated with the robotic control software, such that a user may control both the robot and the surgical tool at the same time. In some embodiments, the controller may be separate, and the user may have to guide the robot to the surgical site first, then activate the surgical tool.

In an embodiment, a user input 1702 may be received by a robotic surgical system software 1704. The user input 1702 may be through a mouse, keyboard, joystick or any other input device. In some embodiments the user input may have a haptic feedback loop, providing the user with some sensitivity to what the instrument may encounter inside a patient. In an embodiment, the robotic surgical system software 1704 may include a software motion planner 1706 for planning the approach of the robotic limbs toward, or into a surgical site. The instructions from the software motion planner 1706 may go through a negative feedback process 1708a and then a software controller 1710a. The software controller 1710a may then properly determine how much movement may be required by the motor/actuator 1712a to properly move the surgical tool, the asymmetric gear assembly or other actuator attached to the surgical tool. For example, the determination may be made based on the sizes or shapes of the respective gears in the asymmetric gear assembly. Motion of the motor/actuator 1712a may be determined through monitoring of an encoder/sensor 1714a with the actual motion of the motor or actuator measured, and reported back to the negative feedback process 1708a. In this way the position of the motor/actuator 1712a may be determined with confidence, and the device output 1716 may be accurately determined, and the safety of the procedure may be monitored. In an embodiment, the robotic surgical system may include a tutorial module for heling a user understand how the robot surgical system and surgical tool combination may be used.

In an embodiment, each software controller 1710a-d may be in electronic communication with a corresponding subtraction process 1708a-d, a software controller 1710a-d controlling a like number of motor/actuators 1712a-d, for example by providing operation control via means such as electrical signals to the motor/actuators 1712a-d, with feedback through at least one corresponding encoder/sensor 1714a-d. The various software controllers 1710a-d and motor/actuators 1712a-d may operate cooperatively to move the device output 1716 properly. In an embodiment, there may be four software controllers, motor/actuator, encoder/sensor and subtraction processes for the asymmetric gear assembly. In some embodiments there may be more.

In an embodiment, the asymmetric gear set and/or the surgical tool may be incorporated into a robotic surgical device. The asymmetric gear set may be controlled through the pulley housing, and a motor assembly. The various motors that may drive and operate the surgical tool may be computer controlled as part of a larger computer controlled robotic system. In some embodiments the computer controller may control the entire robotic system. In some embodiments, the computer controller may provide robotic assistance, allowing a user to manipulate a mechanical arm, and have a robot provide power and assistance to the manipulation.

In some embodiments, the robotic surgical system may have a computer controller. The computer controller may have an operating system, and a series of programs stored on a persistent memory. The programs provide the computer with the necessarily machine instructions to coordinate the movement of the robot elements, and surgical tool elements, and the asymmetric gear set elements.

In various embodiments, the asymmetric gear assembly and surgical tool of the present disclosure may be used for a variety of surgical procedures. The profile of the surgical tool in some embodiments may be 15 mm or less in cross section. In some embodiments, the cross section may be less than 10 mm. In still other embodiments, the cross section may be less than 8 mm. The small cross section may allow the surgical tool to be used in surgeries where space may be limited. In some embodiments, the surgical tool may be used for vertebroplasty and kyphoplasty, spinal laminectomy, spinal decompression, discectomy, foraminotomy, nucleoplasty, spinal fusion or artificial disk replacement. In some embodiments, the surgical tool may be used in lumbar spinal fusion procedures, such as XLIF (extreme lateral interbody fusion), LLIF (lateral lumbar interbody fusion), TLIF (transforaminal lumbar interbody fusion), PLIF (posterior lumbar interbody fusion), endoscopic spine surgeries or any other form of surgery (not necessarily spine surgery) where a small instrument may be desired.

Non-limiting aspects are now provided:

1. An apparatus for use with a robotic tool, the apparatus comprising:
   a first set of prongs disposed along a first axis;
   a second set of prongs disposed along a second axis, the second axis being different from the first axis;
   an asymmetric gear set comprising:
   a rotatable first drive gear disposed on one of the first set of prongs and having a first diameter;
   a rotatable first actuator gear disposed on one of the second set of prongs and having the first diameter, wherein the first drive gear and first actuator gear are in mechanical communication such that the first drive gear is configured to drive the first actuator gear, the first drive gear and the first actuator gear forming a first gear pair;

a rotatable second drive gear disposed on one of the first set of prongs and having a second diameter, the second diameter being different from the first diameter; and a rotatable second actuator gear disposed on one of the second set of prongs and having the second diameter, wherein the second drive gear and the second actuator gear are in mechanical communication such that the second drive gear is configured to drive the second actuator gear, the second drive gear and the second actuator gear forming a second gear pair.

2. The apparatus of aspect 1, further comprising:
a restraint mechanism configured to restrain axial movements of the asymmetric gear set.

3. The apparatus of aspect 2, wherein the restraint mechanism comprises:
a block;
a housing having at least one aperture, wherein a wrist gear is mechanically engaged to one of the first set of prongs through the at least one aperture,
wherein the first set of prongs comprises a first prong and a second prong;
wherein the first prong and the second prong are disposed on opposite sides of the block.

4. The apparatus of aspect 3, further comprising a wrist cable configured to connect the wrist gear to a wrist drive spool.

5. The apparatus of aspect 3, further comprising a rotatable base mechanically coupled to the asymmetric gear set.

6. The apparatus of aspect 5, further comprising a base cable, the base cable configured to connect the rotatable base to a base spool.

7. The apparatus of aspect 5, wherein the rotatable base comprises a first tab and a second tab, wherein the apparatus is configured to rotate about the first axis while rotationally engaged to the first and second tabs.

8. The apparatus of aspect 1, wherein the first drive gear is movable by a first drive cable, the first drive cable is configured to connect the first drive gear to a first drive spool; wherein the second drive gear is movable by a second drive cable, the second drive cable is configured to connect the second drive gear to a second drive spool.

9. The apparatus of aspect 1, wherein the first actuator gear is configured to connect to a first actuator.

10. The apparatus of aspect 1, wherein the second actuator gear is configured to connect to a second actuator.

11. The apparatus of aspect 1, wherein one or more of the first drive gear, the first actuator gear, the second drive gear, or the second actuator gear of the asymmetric gear set include one or more beveled gears.

12. The apparatus of aspect 1, wherein the first diameter is smaller than the second diameter.

13. The apparatus of aspect 1, wherein the first drive gear or the first actuator gear of the first gear pair is made of a different material than the corresponding second drive gear or the second actuator gear of the second gear pair.

14. A minimally invasive surgical tool comprising:
a joint, the joint having a first pair of prongs disposed along a first axis and a second pair of prongs disposed along a second axis, the second axis being different from the first axis;
a first drive gear positioned on a first prong of the first pair of prongs, the first drive gear having a first diameter;

a second drive gear positioned on a second prong of the first pair of prongs, the second drive gear having a second diameter, the second diameter being different from the first diameter;
a first actuator gear positioned on a first prong of the second pair of prongs, the first actuator gear having the first diameter;
a second actuator gear positioned on a second prong of the second pair of prongs, the second actuator gear having the second diameter.
a first actuator coupled to the first actuator gear, the first actuator rotatable in response to movement of the first actuator gear;
a second actuator coupled to the second actuator gear, the second actuator rotatable in response to movement of the second actuator gear; and
a base having a set of tabs extending therefrom, the set of tabs mechanically coupled to the first pair of prongs, and the base rotatable about a third axis, the third axis different from the first axis and the second axis, wherein the first set of prongs are mechanically engaged to the set of tabs,
wherein the first and second actuator are movable in six degrees of freedom by rotating the first and second actuators around the first, second, or third axis.

15. The minimally invasive surgical tool of aspect 14, further comprising:
a housing fittingly engaged to the joint, such that the first pair of prongs and the second pair of prongs protrude from the housing when the joint is placed within the housing.

16. The minimally invasive surgical tool of aspect 14, wherein the first diameter is greater than the second diameter.

17. The minimally invasive surgical tool of aspect 14, wherein the second diameter is greater than the first diameter.

18. A surgical system comprising:
a surgical apparatus including:
a first set of prongs disposed along a first axis;
a second set of prongs disposed along a second axis, the second axis being different from the first axis; and
an asymmetric gear set comprising:
a rotatable first drive gear disposed on one of the first set of prongs,
a rotatable first actuator gear disposed on one of the second set of prongs, wherein the first drive gear and first actuator gear are in mechanical communication such that the first drive gear is configured to drive the first actuator gear, the first drive gear and the first actuator gear forming a first gear pair,
a rotatable second drive gear disposed on one of the first set of prongs, the second diameter being different from the first diameter, and
a rotatable second actuator gear disposed on one of the second set of prongs, wherein the second drive gear and the second actuator gear are in mechanical communication such that the second drive gear is configured to drive the second actuator gear, the second drive gear and the second actuator gear forming a second gear pair;
a first drive cable movably connecting the first drive gear to a first drive spool;
a second drive cable movably connecting the second drive gear to a second drive spool; and
a controller operably coupled with the first drive spool and the second drive spool, the controller configured to:
determine a rotation and movement of each of the first gear pair and the second gear pair based on a respective size of the first gear pair and the second gear pair, and provide operation control of the first drive cable and the second drive cable based on the determined rotation of the first and second drive spools.

19. The surgical system of aspect 18, further comprising:
   a first motor assembly electrically coupled with the controller and mechanically coupled with the first drive cable, the first motor assembly configured to control the first drive cable based on the operation control provided by the controller; and
   a second motor assembly electrically coupled with the controller and mechanically coupled with the second drive cable, the second motor assembly configured to control the second drive cable based on the operation control provided by the controller.

20. The surgical system of aspect 18, further comprising:
   a block; and
   a housing having at least one aperture, wherein a wrist gear is mechanically engaged to one of the first set of prongs through the at least one aperture, wherein the first set of prongs comprising a first prong and a second prong, and wherein the first prong and the second prong are disposed on opposite sides of the block.

21. The surgical system of aspect 18, wherein the first drive gear has a first diameter and the second drive gear has a second diameter, wherein the first diameter is different from the second diameter.

Embodiments of the subject matter and the operations described in this specification may be implemented in digital electronic circuitry, or in computer software, firmware, or hardware, including the structures disclosed in this specification and their structural equivalents, or in combinations of one or more of them. Embodiments of the subject matter described in this specification may be implemented as one or more computer programs, i.e., one or more modules of computer program instructions, encoded on one or more computer storage medium for execution by, or to control the operation of, data processing apparatus, such as a processing circuit. A controller or processing circuit such as CPU may comprise any digital and/or analog circuit components configured to perform the functions described herein, such as a microprocessor, microcontroller, application-specific integrated circuit, programmable logic, etc. Alternatively, or in addition, the program instructions may be encoded on an artificially generated propagated signal, e.g., a machine-generated electrical, optical, or electromagnetic signal, that is generated to encode information for transmission to suitable receiver apparatus for execution by a data processing apparatus.

A computer storage medium may be, or be included in, a computer-readable storage device, a computer-readable storage substrate, a random or serial access memory array or device, or a combination of one or more of them. Moreover, while a computer storage medium is not a propagated signal, a computer storage medium may be a source or destination of computer program instructions encoded in an artificially generated propagated signal. The computer storage medium may also be, or be included in, one or more separate components or media (e.g., multiple CDs, disks, or other storage devices). Accordingly, the computer storage medium is both tangible and non-transitory.

The operations described in this specification may be implemented as operations performed by a data processing apparatus on data stored on one or more computer-readable storage devices or received from other sources. The term "data processing apparatus" or "computing device" encompasses all kinds of apparatus, devices, and machines for processing data, including by way of example a programmable processor, a computer, a system on a chip, or multiple ones, or combinations, of the foregoing The apparatus may include special purpose logic circuitry, e.g., an FPGA (field programmable gate array) or an ASIC (application specific integrated circuit). The apparatus may also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment may realize various different computing model infrastructures, such as web services, distributed computing and grid computing infrastructures.

A computer program (also known as a program, software, software application, script, or code) may be written in any form of programming language, including compiled or interpreted languages, declarative or procedural languages, and it may be deployed in any form, including as a stand-alone program or as a module, component, subroutine, object, or other unit suitable for use in a computing environment. A computer program may, but need not, correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform actions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, embodiments of the subject matter described in this specification may be implemented on a computer having a display device, e.g., a CRT (cathode ray tube) or LCD (liquid crystal display) monitor, OLED (organic light emitting diode) monitor or other form of display for displaying information to the user and a keyboard and/or a pointing device, e.g., a mouse or a trackball, by which the user may provide input to the computer. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input. In addition, a computer may interact with a user by sending documents to and receiving documents from a device that is used by the user; for example, by sending web pages to a web browser on a user's client device in response to requests received from the web browser.

While this specification contains many specific embodiment details, these should not be construed as limitations on the scope of any embodiments or of what may be claimed, but rather as descriptions of features specific to particular embodiments. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

Having described certain embodiments of the methods and systems, it will now become apparent to one of skill in the art that other embodiments incorporating the concepts may be used. It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C#, PROLOG, or in any byte code language such as JAVA. The software programs may be stored on or in one or more articles of manufacture as object code.

The various descriptions and figures of the surgical tool and the asymmetric gear assembly may be taken as generally informative and provide guidance on the use, manufacture and operation of the present disclosure. However, the description and figures should not be taken as limiting in any sense, as the description may be defined by the appended claims.

What is claimed is:
1. An apparatus for use with a robotic tool, the apparatus comprising:
   a first set of prongs disposed along a first axis;
   a second set of prongs disposed along a second axis, the second axis being different from the first axis;
   an asymmetric gear set comprising:
      a rotatable first drive gear disposed on one of the first set of prongs and having a first diameter;
      a rotatable first actuator gear disposed on one of the second set of prongs and having the first diameter, wherein the first drive gear and first actuator gear are in mechanical communication such that the first drive gear is configured to drive the first actuator gear, the first drive gear and the first actuator gear forming a first gear pair;
      a rotatable second drive gear disposed on one of the first set of prongs and having a second diameter, the second diameter being different from the first diameter; and
      a rotatable second actuator gear disposed on one of the second set of prongs and having the second diameter, wherein the second drive gear and the second actuator gear are in mechanical communication such that the second drive gear is configured to drive the second actuator gear, the second drive gear and the second actuator gear forming a second gear pair.

2. The apparatus of claim 1, further comprising:
a restraint mechanism configured to restrain axial movements of the asymmetric gear set.

3. The apparatus of claim 2, wherein the restraint mechanism comprises:
a block;
a housing having at least one aperture, wherein a wrist gear is mechanically engaged to one of the first set of prongs through the at least one aperture,
wherein the first set of prongs comprises a first prong and a second prong;
wherein the first prong and the second prong are disposed on opposite sides of the block.

4. The apparatus of claim 3, further comprising a wrist cable configured to connect the wrist gear to a wrist drive spool.

5. The apparatus of claim 3, further comprising a rotatable base mechanically coupled to the asymmetric gear set.

6. The apparatus of claim 5, further comprising a base cable, the base cable configured to connect the rotatable base to a base spool.

7. The apparatus of claim 5, wherein the rotatable base comprises a first tab and a second tab, wherein the apparatus is configured to rotate about the first axis while rotationally engaged to the first and second tabs.

8. The apparatus of claim 1, wherein the first drive gear is movable by a first drive cable, the first drive cable is configured to connect the first drive gear to a first drive spool; wherein the second drive gear is movable by a second drive cable, the second drive cable is configured to connect the second drive gear to a second drive spool.

9. The apparatus of claim 1, wherein the first actuator gear is configured to connect to a first actuator.

10. The apparatus of claim 1, wherein the second actuator gear is configured to connect to a second actuator.

11. The apparatus of claim 1, wherein one or more of the first drive gear, the first actuator gear, the second drive gear, or the second actuator gear of the asymmetric gear set include one or more beveled gears.

12. The apparatus of claim 1, wherein the first diameter is smaller than the second diameter.

13. The apparatus of claim 1, wherein the first drive gear or the first actuator gear of the first gear pair is made of a different material than the corresponding second drive gear or the second actuator gear of the second gear pair.

14. A minimally invasive surgical tool comprising:
a joint, the joint having a first pair of prongs disposed along a first axis and a second pair of prongs disposed along a second axis, the second axis being different from the first axis;
a first drive gear positioned on a first prong of the first pair of prongs, the first drive gear having a first diameter;
a second drive gear positioned on a second prong of the first pair of prongs, the second drive gear having a second diameter, the second diameter being different from the first diameter;
a first actuator gear positioned on a first prong of the second pair of prongs, the first actuator gear having the first diameter;
a second actuator gear positioned on a second prong of the second pair of prongs, the second actuator gear having the second diameter;
a first actuator coupled to the first actuator gear, the first actuator rotatable in response to movement of the first actuator gear;
a second actuator coupled to the second actuator gear, the second actuator rotatable in response to movement of the second actuator gear; and
a base having a set of tabs extending therefrom, the set of tabs mechanically coupled to the first pair of prongs, and the base rotatable about a third axis, the third axis different from the first axis and the second axis, wherein the first set of prongs are mechanically engaged to the set of tabs,
wherein the first and second actuator are movable in six degrees of freedom by rotating the first and second actuators around the first, second, or third axis.

15. The minimally invasive surgical tool of claim 14, further comprising:
a housing fittingly engaged to the joint, such that the first pair of prongs and the second pair of prongs protrude from the housing when the joint is placed within the housing.

16. The minimally invasive surgical tool of claim 14, wherein the first diameter is greater than the second diameter.

17. The minimally invasive surgical tool of claim 14, wherein the second diameter is greater than the first diameter.

18. A surgical system comprising:
a surgical apparatus including:
a first set of prongs disposed along a first axis;
a second set of prongs disposed along a second axis, the second axis being different from the first axis; and
an asymmetric gear set comprising:
a rotatable first drive gear disposed on one of the first set of prongs, the first drive rear having a first diameter,
a rotatable first actuator gear disposed on one of the second set of prongs, the first actuator rear having the first diameter, wherein the first drive gear and first actuator gear are in mechanical communication such that the first drive gear is configured to drive the first actuator gear, the first drive gear and the first actuator gear forming a first gear pair,
a rotatable second drive gear disposed on one of the first set of prongs, the second drive rear having a second diameter, the second diameter being different from the first diameter, and
a rotatable second actuator gear disposed on one of the second set of prongs, the second actuator rear having the second diameter, wherein the second drive gear and the second actuator gear are in mechanical communication such that the second drive gear is configured to drive the second actuator gear, the second drive gear and the second actuator gear forming a second gear pair;
a first drive cable movably connecting the first drive gear to a first drive spool;
a second drive cable movably connecting the second drive gear to a second drive spool; and
a controller operably coupled with the first drive spool and the second drive spool, the controller configured to:
determine a rotation and movement of each of the first gear pair and the second gear pair based on a respective size of the first gear pair and the second gear pair, and
provide operation control of the first drive cable and the second drive cable based on the determined rotation of the first and second drive spools.

19. The surgical system of claim 18, further comprising:
a first motor assembly electrically coupled with the controller and mechanically coupled with the first drive cable, the first motor assembly configured to control the first drive cable based on the operation control provided by the controller; and
a second motor assembly electrically coupled with the controller and mechanically coupled with the second drive cable, the second motor assembly configured to control the second drive cable based on the operation control provided by the controller.

20. The surgical system of claim 18, further comprising:
a block; and
a housing having at least one aperture, wherein a wrist gear is mechanically engaged to one of the first set of prongs through the at least one aperture, wherein the first set of prongs comprising a first prong and a second prong, and wherein the first prong and the second prong are disposed on opposite sides of the block.

21. The surgical system of claim 18, wherein the first diameter is smaller than the second diameter.

* * * * *